(12) United States Patent
Somerville et al.

(10) Patent No.: US 7,241,878 B1
(45) Date of Patent: Jul. 10, 2007

(54) **MODIFIED CELLULOSE SYNTHASE GENE FROM *ARABIDOPSIS THALIANA* CONFERS HERBICIDE RESISTANCE TO PLANTS**

(75) Inventors: Chris R. Somerville, Portola Valley, CA (US); Wolf Scheible, Golm (DE)

(73) Assignee: U.S. Department of Energy, Washington, DC (US)

( * ) Notice: Subject to any disclaimer, the term of this patent is extended or adjusted under 35 U.S.C. 154(b) by 496 days.

(21) Appl. No.: 10/721,996

(22) Filed: Nov. 26, 2003

Related U.S. Application Data

(63) Continuation-in-part of application No. 09/686,234, filed on Oct. 11, 2000, now abandoned.

(60) Provisional application No. 60/159,369, filed on Oct. 14, 1999.

(51) Int. Cl.
| | |
|---|---|
| C07H 21/04 | (2006.01) |
| C12P 15/04 | (2006.01) |
| C12N 9/44 | (2006.01) |
| C12N 15/82 | (2006.01) |
| A01H 1/02 | (2006.01) |
| A01H 1/00 | (2006.01) |
| A01H 5/00 | (2006.01) |

(52) U.S. Cl. .................. 536/23.2; 435/91.1; 435/209; 435/69.1; 800/265; 800/279; 800/280; 800/300

(58) Field of Classification Search .............. 435/209, 435/419, 69.1, 320.1
See application file for complete search history.

(56) References Cited

U.S. PATENT DOCUMENTS 6,495,740 B1 * 12/2002 Arioli et al. ................ 800/284

OTHER PUBLICATIONS

Heim et al., A second locus, lxr B1 in *Arabidopsis thaliana*, that confers resitance to the herbicide isoxaben . Plant Physiol. , 1990 vol. 92 : 858-861.*
Scheible et al., Modifications of cellulose synthase confer resistance to isoxaben and thiazolidinione herbicides in *Arabidopsis* lxr1 mutants. PNAS., 2001, vol. 98 (18): 1079-10084.*
"Modifications of Cellulose Synthase Confer Resistance to Isoxaben and Thiazolidinone Herbicides in *Arabidopsis* lxrl Mutants", scheible, Wolf-Rudiger, et al., *Proc. Natl. Acad. Sci.* vol. 98:18:10079-10084, Aug. 28, 2001.

* cited by examiner

Primary Examiner—Rebecca E. Prouty
Assistant Examiner—Ganapathirama Raghu
(74) Attorney, Agent, or Firm—Brian J. Lally; Daniel D. Park; Paul A. Gottlieb

(57) ABSTRACT

Cellulose synthase ("CS"), a key enzyme in the biosynthesis of cellulose in plants is inhibited by herbicides comprising thiazolidinones such as 5-tert-butyl-carbamoyloxy-3-(3-tri-fluromethyl)phenyl-4-thiazolidinone (TZ), isoxaben and 2,6-dichlorobenzonitrile (DCB). Two mutant genes encoding isoxaben and TZ-resistant cellulose synthase have been isolated from isoxaben and TZ-resistant *Arabidopsis thaliana* mutants. When compared with the gene coding for isoxaben or TZ-sensitive cellulose synthase, one of the resistant CS genes contains a point mutation, wherein glycine residue 998 is replaced by an aspartic acid. The other resistant mutation is due to a threonine to isoleucine change at amino acid residue 942. The mutant CS gene can be used to impart herbicide resistance to a plant; thereby permitting the utilization of the herbicide as a single application at a concentration which ensures the complete or substantially complete killing of weeds, while leaving the transgenic crop plant essentially undamaged.

2 Claims, 1 Drawing Sheet

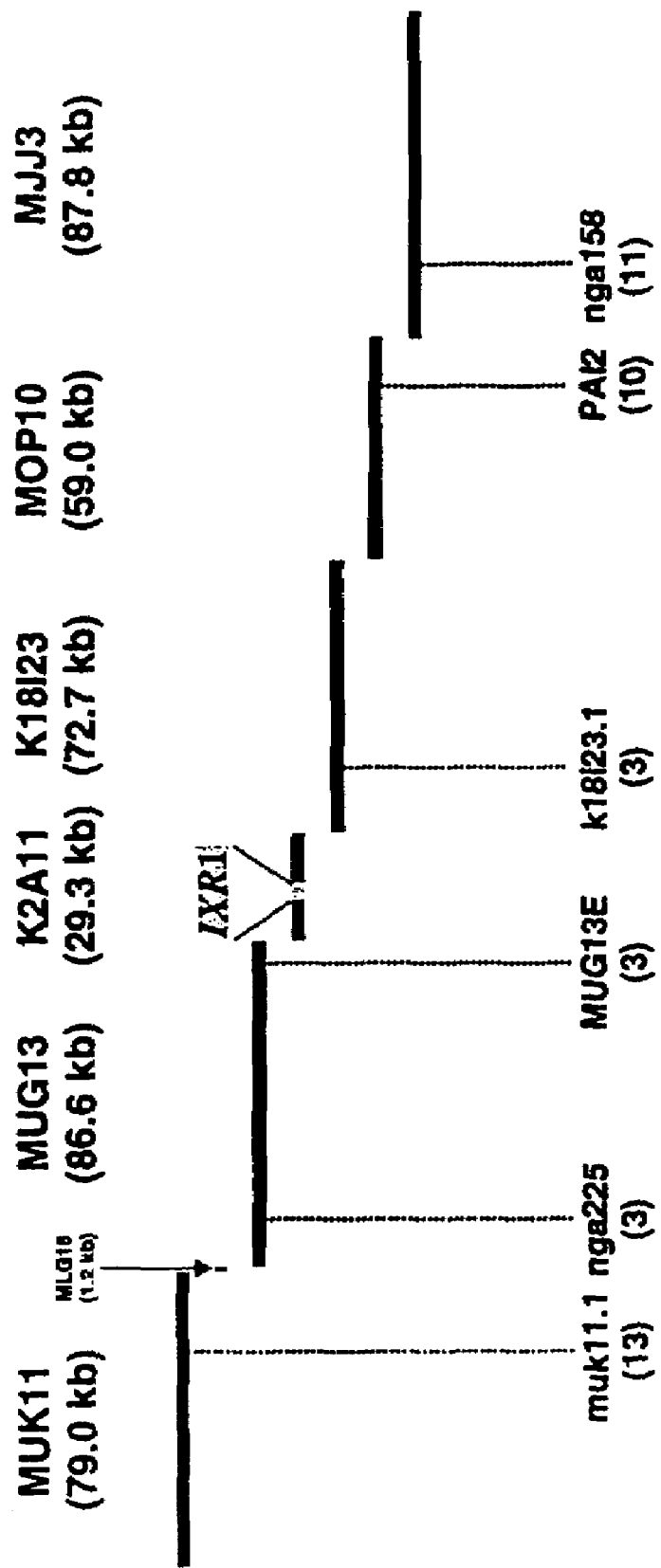
Figure 1: Map position of IXR1 gene on chromosome 5

SEQUENCE LISTING

<160> NUMBER OF SEQ ID NOS: 32

<210> SEQ ID NO 1
<211> LENGTH: 3563
<212> TYPE: DNA
<213> ORGANISM: Arabidopsis thaliana

<400> SEQUENCE: 1

```
atcccaagat tctcctcttc gtcttcctta taaactatct ctctgtagag aagaaagctt      60
ggatccagat tgagagagat tcagagagcc acatcaccac actccatctt cagatctcat     120
gatttgaact attccgacgt ttcggtgttg gaagcaacta agtgacaaat ggaatccgaa     180
ggggaaaccg cgggaaagcc gatgaagaac attgttccgc agacttgcca gatctgtagt     240
gacaatgttg gcaagactgt tgatggagat cgttttgtgg cttgtgatat ttgttcattc     300
ccagtttgtc ggccttgcta cgagtatgag aggaaagatg ggaatcaatc ttgtcctcag     360
```

-continued

| | |
|---|---|
| tgcaaaacca gatacaagag gctcaaaggt agtcctgcta ttcctggtga taaagacgag | 420 |
| gatggcttag ctgatgaagg tactgttgag ttcaactacc ctcagaagga gaaaatttca | 480 |
| gagcggatgc ttggttggca tcttactcgt gggaagggag aggaaatggg ggaaccccag | 540 |
| tatgataaag aggtctctca caatcatctt cctcgtctca cgagcagaca agatacttca | 600 |
| ggagagtttt ctgctgcctc acctgaacgc ctctctgtat cttctactat cgctggggga | 660 |
| aagcgccttc cctattcatc agatgtcaat caatcaccaa atagaaggat gtggatcct | 720 |
| gttggactcg ggaatgtagc ttggaaggag agagttgatg ctggaaaat gaagcaagag | 780 |
| aagaatactg gtcctgtcag cacgcaggct gcttctgaaa gaggtggagt agatattgat | 840 |
| gccagcacag atatcctagc agatgaggct ctgctgaatg acgaagcgag gcagcctctg | 900 |
| tcaaggaaag tttcaattcc ttcatcacgg atcaatcctt acagaatggt tattatgctg | 960 |
| cggcttgtta tcctttgtct cttcttgcat taccgtataa caaacccagt gccaaatgcc | 1020 |
| tttgctctat ggctggtctc tgtgatatgt gagatctggt ttgccttatc ctggattttg | 1080 |
| gatcagtttc ccaagtggtt tcctgtgaac cgtgaaacct acctcgacag gcttgcttta | 1140 |
| agatatgatc gtgaaggtga gccatcacag ttagctgctg ttgacatttt cgtgagtact | 1200 |
| gttgacccct tgaaggagcc acccttgtg acagccaaca cagtgctctc tattctggct | 1260 |
| gttgactacc cagttgacaa ggtgtcctgt tatgttttg atgatggtgc tgctatgtta | 1320 |
| tcatttgaat cacttgcaga acatcagag tttgctcgta atgggtacc attttgcaag | 1380 |
| aaatatagca tagagcctcg tgcaccagaa tggtactttg ctgcgaaaat agattacttg | 1440 |
| aaggataaag ttcagacatc atttgtcaaa gatcgtagag ctatgaagag ggaatatgag | 1500 |
| gaatttaaaa tccgaatcaa tgcacttgtt tccaaagccc taaaatgtcc tgaagaaggg | 1560 |
| tgggttatgc aagatggcac accgtggcct ggaaataata caggggacca tccaggaatg | 1620 |
| atccaggtct tcttagggca aaatggtgga cttgatgcag agggcaatga gctcccgcgt | 1680 |
| ttggtatatg tttctcgaga aaagcgacca ggattccagc accacaaaaa ggctggtgct | 1740 |
| atgaatgcac tggtgagagt ttcagcagtt cttaccaatg gacctttcat cttgaatctt | 1800 |
| gattgtgatc attacataaa taacagcaaa gccttaagag aagcaatgtg cttcctgatg | 1860 |
| gacccaaacc tcgggaagca agtttgttat gttcagttcc cacaaagatt tgatggtatc | 1920 |
| gataagaacg atagatatgc taatcgtaat accgtgttct ttgatattaa cttgagaggt | 1980 |
| ttagatggga ttcaaggacc tgtatatgtc ggaactggat gtgttttcaa cagaacagca | 2040 |
| ttatacggtt atgaacctcc aataaaagta aaacacaaga agccaagtct tttatctaag | 2100 |
| ctctgtggtg gatcaagaaa gaagaattcc aaagctaaga aagagtcgga caaaaagaaa | 2160 |
| tcaggcaggc atactgactc aactgttcct gtattcaacc tcgatgacat agaagaggga | 2220 |
| gttgaaggtg ctggttttga tgatgaaaag gcgctcttaa tgtcgcaaat gagcctggag | 2280 |
| aagcgatttg gacagtctgc tgttttgtt gcttctaccc taatgaaaaa tggtggtgtt | 2340 |
| cctccttcag caactccaga aaaccttctc aaagaggcta tccatgtcat tagttgtggt | 2400 |
| tatgaggata agtcagattg gggaatggag attggatgga tctatggttc tgtgacagaa | 2460 |
| gatattctga ctgggttcaa aatgcatgcc cgtggatggc gatccattta ctgcatgcct | 2520 |
| aagcttccag ctttcaaggg ttctgctcct atcaatcttt cagatcgtct gaaccaagtg | 2580 |
| ctgaggtggg ctttaggttc agttgagatt ctcttcagtc ggcattgtcc tatatggtat | 2640 |
| ggttacaatg ggaggctaaa attcttgag aggtttgcgt atgtgaacac caccatctac | 2700 |
| cctatcacct ccattcctct tctcatgtat tgtacattgc tagccgtttg tctcttcacc | 2760 |

-continued

```
aaccagttta ttattcctca gattagtaac attgcaagta tatggtttct gtctctcttt    2820
ctctccattt tcgccacggg tatactagaa atgaggtgga gtggcgtagg catagacgaa    2880
tggtggagaa cgagcagtt tgggtcatt ggtggagtat ccgctcattt attcgctgtg    2940
tttcaaggta tcctcaaagt ccttgccggt attgacacaa acttcacagt tacctcaaaa    3000
gcttcagatg aagacggaga ctttgctgag ctctacttgt tcaaatggac aacacttctg    3060
attccgccaa cgacgctgct cattgtaaac ttagtgggag ttgttgcagg agtctcttat    3120
gctatcaaca gtggatacca atcatgggga ccactctttg ataagttgtt ctttgccttc    3180
tgggtgattg ttcacttgta ccctttcctc aagggtttga tgggtcgaca gaaccggact    3240
cctaccattg ttgtggtctg gtctgttctc ttggcttcta tcttctcgtt gttgtgggtt    3300
aggattgatc ccttcactag ccgagtcact ggcccggaca ttctggaatg tggaatcaac    3360
tgttgagaag cgagcaaata tttacctgtt tgagggtta aaaaaaacac agaatttaaa    3420 ttattttttca ttgtttttatt tgttcacttt tttactttg ttgtgtgtat ctgtctgttc    3480
gttcttctgt cttggtgtca taaatttatg tgtagaatat atcttactct agttactttg    3540
gaaagttata attaaagtga aag                                             3563
```

<210> SEQ ID NO 2
<211> LENGTH: 3563
<212> TYPE: DNA
<213> ORGANISM: Arabidopsis thaliana

<400> SEQUENCE: 2

```
atcccaagat tctcctcttc gtcttcctta taaactatct ctctgtagag aagaaagctt      60
ggatccagat tgagagagat tcagagagcc acatcaccac actccatctt cagatctcat     120
gatttgaact attccgacgt ttcggtgttg aagcaacta agtgacaaat ggaatccgaa     180
ggggaaaccg cgggaaagcc gatgaagaac attgttccgc agacttgcca gatctgtagt     240
gacaatgttg gcaagactgt tgatggagat cgttttgtgg cttgtgatat tgttcattc      300 ccagtttgtc ggccttgcta cgagtatgag aggaaagatg ggaatcaatc ttgtcctcag     360
tgcaaaacca gatacaagag gctcaaaggt agtcctgcta ttcctggtga taaagacgag     420
gatggcttag ctgatgaagg tactgttgag ttcaactacc ctcagaagga gaaaatttca     480
gagcggatgc ttggttggca tcttactcgt gggaagggag aggaaatggg ggaaccccag     540
tatgataaag aggtctctca caatcatctt cctcgtctca cgagcagaca agatacttca     600
ggagagtttt ctgctgcctc acctgaacgc ctctctgtat cttctactat cgctggggga     660
aagcgccttc cctattcatc agatgtcaat caatcaccaa atagaaggat tgtggatcct     720
gttggactcg ggaatgtagc ttggaaggag agagttgatg gctggaaaat gaagcaagag     780
aagaatactg tcctgtcag cacgcaggct gcttctgaaa gaggtggagt agatattgat     840
gccagcacag atatcctagc agatgaggct ctgctgaatg acgaagcgag gcagcctctg     900
tcaaggaaag tttcaattcc ttcatcacgg atcaatcctt acagaatggt tattatgctg     960
cggcttgtta tcctttgtct cttcttgcat taccgtataa caaacccagt gccaaatgcc    1020
tttgctctat ggctggtctc tgtgatatgt gagatctggt ttgccttatc ctggattttg    1080
gatcagtttc ccaagtggtt tcctgtgaac cgtgaaacct acctcgacag gcttgcttta    1140
agatatgatc gtgaaggtga gccatcacag ttagctgctg ttgacatttt cgtgagtact    1200
gttgacccct tgaaggagcc accccttgtg acagccaaca cagtgctctc tattctggct    1260
```

-continued

```
gttgactacc cagttgacaa ggtgtcctgt tatgttttg atgatggtgc tgctatgtta    1320
tcatttgaat cacttgcaga acatcagag tttgctcgta aatgggtacc atttttgcaag    1380 aaatatagca tagagcctcg tgcaccagaa tggtactttg ctgcgaaaat agattacttg   1440
aaggataaag ttcagacatc atttgtcaaa gatcgtagag ctatgaagag ggaatatgag   1500
gaatttaaaa tccgaatcaa tgcacttgtt tccaaagccc taaaatgtcc tgaagaaggg   1560
tgggttatgc aagatggcac accgtggcct ggaaataata caggggacca tccaggaatg   1620
atccaggtct tcttagggca aaatggtgga cttgatgcag agggcaatga gctcccgcgt   1680
ttggtatatg tttctcgaga aaagcgacca ggattccagc accacaaaaa ggctggtgct   1740
atgaatgcac tggtgagagt ttcagcagtt cttaccaatg gacctttcat cttgaatctt   1800
gattgtgatc attacataaa taacagcaaa gccttaagag aagcaatgtg cttcctgatg   1860
gacccaaacc tcgggaagca agtttgttat gttcagttcc cacaaagatt tgatggtatc   1920
gataagaacg atagatatgc taatcgtaat accgtgttct ttgatattaa cttgagaggt   1980
ttagatggga ttcaaggacc tgtatatgtc ggaactggat gtgttttcaa cagaacagca   2040
ttatacggtt atgaacctcc aataaaagta aacacaaga agccaagtct tttatctaag    2100
ctctgtggtg gatcaagaaa gaagaattcc aaagctaaga aagagtcgga caaaaagaaa   2160
tcaggcaggc atactgactc aactgttcct gtattcaacc tcgatgacat agaagaggga   2220
gttgaaggtg ctggttttga tgatgaaaag gcgctcttaa tgtcgcaaat gagcctggag   2280
aagcgatttg acagtctgc tgttttgtt gcttctaccc taatgaaaaa tggtggtgtt    2340
cctccttcag caactccaga aaaccttctc aaagaggcta tccatgtcat tagttgtggt   2400
tatgaggata agtcagattg gggaatggag attggatgga tctatggttc tgtgacagaa   2460
gatattctga ctgggttcaa aatgcatgcc cgtggatggc gatccattta ctgcatgcct   2520
aagcttccag cttcaagg ttctgctcct atcaatctt cagatcgtct gaaccaagtg     2580
ctgaggtggg ctttaggttc agttgagatt ctcttcagtc ggcattgtcc tatatggtat   2640
ggttacaatg ggaggctaaa atttcttgag aggtttgcgt atgtgaacac caccatctac   2700
cctatcacct ccattcctct tctcatgtat tgtacattgc tagccgtttg tctcttcacc   2760
aaccagttta ttattcctca gattagtaac attgcaagta tatggtttct gtctctcttt   2820
ctctccattt tcgccacggg tatactagaa atgaggtgga gtggcgtagg catagacgaa   2880
tggtggagaa cgagcagtt ttgggtcatt ggtggagtat ccgctcattt attcgctgtg    2940
tttcaaggta tcctcaaagt ccttgccggt attgacacaa acttcacagt tatctcaaaa   3000
gcttcagatg aagacggaga ctttgctgag ctctacttgt tcaaatggac aacacttctg   3060
attccgccaa cgacgctgct cattgtaaac ttagtgggag ttgttgcagg agtctcttat   3120
gctatcaaca gtggatacca atcatgggga ccactctttg gtaagttgtt ctttgccttc   3180
tgggtgattg ttcacttgta cccttttcctc aagggtttga tgggtcgaca gaaccggact   3240
cctaccattg ttgtggtctg gtctgttctc ttggcttcta tcttctcgtt gttgtgggtt   3300
aggattgatc ccttcactag ccgagtcact ggcccggaca ttctggaatg tggaatcaac   3360
tgttgagaag cgagcaaata tttacctgtt ttgagggtta aaaaaaacac agaatttaaa   3420
ttatttttca ttgtttttatt tgttcacttt tttacttttg ttgtgtgtat ctgtctgttc   3480
gttcttctgt cttggtgtca taaatttatg tgtagaatat atcttactct agttactttg   3540
gaaagttata attaaagtga aag                                           3563
```

```
<210> SEQ ID NO 3
<211> LENGTH: 3563
<212> TYPE: DNA
<213> ORGANISM: Artificial
<220> FEATURE:
<223> OTHER INFORMATION: ixr1-1 mutant variation

<400> SEQUENCE: 3
atcccaagat tctcctcttc gtcttcctta taaactatct ctctgtagag aagaaagctt      60
ggatccagat tgagagagat tcagagagcc acatcaccac actccatctt cagatctcat     120
gatttgaact attccgacgt ttcggtgttg aagcaacta agtgacaaat ggaatccgaa      180
ggggaaaccg cgggaaagcc gatgaagaac attgttccgc agacttgcca gatctgtagt    240
gacaatgttg gcaagactgt tgatggagat cgttttgtgg cttgtgatat ttgttcattc    300
ccagtttgtc ggccttgcta cgagtatgag aggaaagatg ggaatcaatc ttgtcctcag    360
tgcaaaacca gatacaagag gctcaaaggt agtcctgcta ttcctggtga taaagacgag    420
gatggcttag ctgatgaagg tactgttgag ttcaactacc ctcagaagga gaaaatttca    480
gagcggatgc ttggttggca tcttactcgt gggaagggag aggaaatggg ggaaccccag    540
tatgataaag aggtctctca caatcatctt cctcgtctca cgagcagaca agatacttca    600
ggagagtttt ctgctgcctc acctgaacgc ctctctgtat cttctactat cgctggggga    660
aagcgccttc cctattcatc agatgtcaat caatcaccaa atagaaggat gtggatcct    720 gttggactcg ggaatgtagc ttggaaggag agagttgatg ctggaaaat gaagcaagag    780 aagaatactg gtcctgtcag cacgcaggct gcttctgaaa gaggtggagt agatattgat    840
gccagcacag atatcctagc agatgaggct ctgctgaatg acgaagcgag gcagcctctg    900
tcaaggaaag tttcaattcc ttcatcacgg atcaatcctt acagaatggt tattatgctg    960
cggcttgtta ccctttgtct cttcttgcat taccgtataa caaacccagt gccaaatgcc   1020
tttgctctat ggctggtctc tgtgatatgt gagatctggt ttgccttatc ctggattttg   1080
gatcagtttc ccaagtggtt tcctgtgaac cgtgaaacct acctcgacag gcttgcttta    1140
agatatgatc gtgaaggtga gccatcacag ttagctgctg ttgacatttt cgtgagtact    1200
gttgacccct tgaaggagcc acccccttgtg acagccaaca cagtgctctc tattctggct   1260
gttgactacc cagttgacaa ggtgtcctgt tatgttttg atgatggtgc tgctatgtta    1320
tcatttgaat cacttgcaga acatcagag tttgctcgta atgggtacc attttgcaag    1380 aaatatagca tagagcctcg tgcaccagaa tggtactttg ctgcgaaaat agattacttg    1440
aaggataaag ttcagacatc atttgtcaaa gatcgtagag ctatgaagag ggaatatgag   1500
gaatttaaaa tccgaatcaa tgcacttgtt tccaaagccc taaaatgtcc tgaagaaggg   1560
tgggttatgc aagatggcac accgtggcct ggaaataata caggggacca tccaggaatg   1620
atccaggtct tcttagggca aaatggtgga cttgatgcag agggcaatga gctcccgcgt    1680
ttggtatatg tttctcgaga aaagcgacca ggattccagc accacaaaaa ggctggtgct   1740
atgaatgcac tggtgagagt ttcagcagtt cttaccaatg gacctttcat cttgaatctt   1800
gattgtgatc attacataaa taacagcaaa gccttaagag aagcaatgtg cttcctgatg   1860
gacccaaacc tcgggaagca agtttgttat gttcagttcc cacaaagatt tgatggtatc   1920
gataagaacg atagatatgc taatcgtaat accgtgttct ttgatattaa cttgagaggt   1980
ttagatggga ttcaaggacc tgtatatgtc ggaactggat gtgttttcaa cagaacagca   2040
ttatacggtt atgaacctcc aataaaagta aaacacaaga agccaagtct tttatctaag   2100
```

```
ctctgtggtg gatcaagaaa gaagaattcc aaagctaaga aagagtcgga caaaaagaaa      2160
tcaggcaggc atactgactc aactgttcct gtattcaacc tcgatgacat agaagaggga      2220
gttgaaggtg ctggttttga tgatgaaaag gcgctcttaa tgtcgcaaat gagcctggag      2280
aagcgatttg gacagtctgc tgttttttgtt gcttctaccc taatgaaaaa tggtggtgtt     2340
cctccttcag caactccaga aaaccttctc aaagaggcta tccatgtcat tagttgtggt      2400
tatgaggata agtcagattg gggaatggag attggatgga tctatggttc tgtgacagaa      2460
gatattctga ctgggttcaa aatgcatgcc cgtggatggc gatccattta ctgcatgcct      2520
aagcttccag ctttcaaggg ttctgctcct atcaatcttt cagatcgtct gaaccaagtg      2580
ctgaggtggg ctttaggttc agttgagatt ctcttcagtc ggcattgtcc tatatggtat      2640
ggttacaatg ggaggctaaa atttcttgag aggtttgcgt atgtgaacac caccatctac      2700
cctatcacct ccattcctct tctcatgtat tgtacattgc tagccgtttg tctcttcacc      2760
aaccagttta ttattcctca gattagtaac attgcaagta tatggttttct gtctctcttt    2820 ctctccattt tcgccacggg tatactagaa atgaggtgga gtggcgtagg catagacgaa      2880
tggtggagaa acgagcagtt tgggtcatt ggtgagtat ccgctcattt attcgctgtg        2940
tttcaaggta tcctcaaagt ccttgccggt attgacacaa acttcacagt tatctcaaaa      3000
gcttcagatg aagacggaga ctttgctgag ctctacttgt tcaaatggac aacacttctg      3060
attccgccaa cgacgctgct cattgtaaac ttagtgggag ttgttgcagg agtctcttat      3120
gctatcaaca gtggatacca atcatgggga ccactctttg ataagttgtt ctttgccttc      3180
tgggtgattg ttcacttgta cccttttcctc aagggtttga tgggtcgaca gaaccggact     3240
cctaccattg ttgtggtctg gtctgttctc ttggcttcta tcttctcgtt gttgtgggtt      3300
aggattgatc ccttcactag ccgagtcact ggcccggaca ttctggaatg tggaatcaac      3360
tgttgagaag cgagcaaata tttacctgtt tgagggtta aaaaaaacac agaatttaaa       3420
ttatttttca ttgtttttatt tgttcacttt tttactttttg ttgtgtgtat ctgtctgttc    3480
gttcttctgt cttggtgtca taaatttatg tgtagaatat atcttactct agttactttg     3540
gaaagttata attaaagtga aag                                              3563

<210> SEQ ID NO 4
<211> LENGTH: 3563
<212> TYPE: DNA
<213> ORGANISM: Artificial
<220> FEATURE:
<223> OTHER INFORMATION: ixr1-1 mutant variant

<400> SEQUENCE: 4
atcccaagat tctcctcttc gtcttcctta taaactatct ctctgtagag aagaaagctt        60
ggatccagat tgagagagat tcagagagcc acatcaccac actccatctt cagatctcat       120
gatttgaact attccgacgt ttcggtgttg aagcaacta agtgacaaat ggaatccgaa        180
ggggaaaccg cgggaaagcc gatgaagaac attgttccgc agacttgcca gatctgtagt       240
gacaatgttg gcaagactgt tgatggagat cgttttgtgg cttgtgatat tgttcattc       300 ccagtttgtc ggccttgcta cgagtatgag aggaaagatg ggaatcaatc ttgtcctcag       360
tgcaaaacca gatacaagag gctcaaaggt agtcctgcta ttcctggtga taagacgag        420 gatggcttag ctgatgaagg tactgttgag ttcaactacc ctcagaagga gaaaatttca      480
gagcggatgc ttggttggca tcttactcgt gggaagggag aggaaatggg ggaaccccag      540
tatgataaag aggtctctca caatcatctt cctcgtctca cgagcagaca agatacttca     600
```

```
ggagagtttt ctgctgcctc acctgaacgc ctctctgtat cttctactat cgctggggga    660
aagcgccttc cctattcatc agatgtcaat caatcaccaa atagaaggat tgtggatcct    720
gttggactcg ggaatgtagc ttggaaggag agagttgatg ctggaaaat gaagcaagag    780 aagaatactg gtcctgtcag cacgcaggct gcttctgaaa gaggtggagt agatattgat    840
gccagcacac atatcctagc agatgaggct ctgctgaatg acgaagcgag gcagcctctg    900
tcaaggaaag tttcaattcc ttcatcacgg atcaatcctt acagaatggt tattatgctg    960
cggcttgtta tcctttgtct cttcttgcat taccgtataa caaacccagt gccaaatgcc    1020
tttgctctat ggctggtctc tgtgatatgt gagatctggt ttgccttatc ctggattttg    1080
gatcagtttc ccaagtggtt tcctgtgaac cgtgaaacct acctcgacag gcttgcttta    1140
agatatgatc gtgaaggtga gccatcacag ttagctgctg ttgacatttt cgtgagtact    1200
gttgacccct tgaaggagcc accccttgtg acagccaaca cagtgctctc tattctggct    1260
gttgactacc cagttgacaa ggtgtcctgt tatgttttg atgatggtgc tgctatgtta    1320
tcatttgaat cacttgcaga acatcagag tttgctcgta atgggtacc attttgcaag    1380 aaatatagca tagagcctcg tgcaccagaa tggtactttg ctgcgaaaat agattacttg    1440
aaggataaag ttcagacatc atttgtcaaa gatcgtagag ctatgaagag gaatatgag    1500 gaatttaaaa tccgaatcaa tgcacttgtt tccaaagccc taaaatgtcc tgaagaaggg    1560
tgggttatgc aagatggcac accgtggcct ggaaataata cagggaccac tccaggaatg    1620
atccaggtct tcttagggca aaatggtgga cttgatgcag agggcaatga gctcccgcgt    1680
ttggtatatg tttctcgaga aaagcgacca ggattccagc accacaaaaa ggctggtgct    1740
atgaatgcac tggtgagagt ttcagcagtt cttaccaatg gacctttcat cttgaatctt    1800
gattgtgatc attacataaa taacagcaaa gccttaagag aagcaatgtg cttcctgatg    1860
gacccaaacc tcgggaagca gtttgttat gttcagttcc cacaaagatt tgatggtatc    1920
gataagaacg atagatatgc taatcgtaat accgtgttct ttgatattaa cttgagaggt    1980
ttagatggga ttcaaggacc tgtatatgtc ggaactggat gtgttttcaa cagaacagca    2040
ttatacggtt atgaacctcc aataaaagta aaacacaaga agccaagtct tttatctaag    2100
ctctgtggtg gatcaagaaa gaagaattcc aaagctaaga aagagtcgga caaaaagaaa    2160
tcaggcaggc atactgactc aactgttcct gtattcaacc tcgatgacat agaagaggga    2220
gttgaaggtc ctggttttga tgatgaaaag gcgctcttaa tgtcgcaaat gagcctggag    2280
aagcgatttg gacagtctgc tgttttttgt gcttctaccc taatggaaaa tggtggtgtt    2340
cctccttcag caactccaga aaaccttctc aaagaggcta tccatgtcat tagttgtggt    2400
tatgaggata agtcagattg gggaatggag attggatgga tctatggttc tgtgacagaa    2460
gatattctga ctgggttcaa aatgcatgcc cgtggatggc gatccattta ctgcatgcct    2520
aagcttccag ctttcaaggg ttctgctcct atcaatcttt cagatcgtct gaaccaagtg    2580
ctgaggtggg ctttaggttc agttgagatt ctcttcagtc ggcattgtcc tatatggtat    2640
ggttacaatg ggaggctaaa atttcttgag aggtttgcgt atgtgaacac caccatctac    2700
cctatcacct ccattcctct tctcatgtat tgtacattgc tagccgtttg tctcttcacc    2760
aaccagttta ttattcctca gattagtaac attgcaagta tggtttct gtctctcttt    2820 ctctccattt tcgccacggg tatactagaa atgaggtgga gtggcgtagg catagacgaa    2880
tggtggagaa acgagcagtt ttgggtcatt ggtggagtat ccgctcattt attcgctgtg    2940
```

-continued

```
tttcaaggta tcctcaaagt ccttgccggt attgacacaa acttcacagt tacctcaaaa   3000
gcttcagatg aagacggaga ctttgctgag ctctacttgt tcaaatggac aacacttctg   3060
attccgccaa cgacgctgct cattgtaaac ttagtgggag ttgttgcagg agtctcttat   3120
gctatcaaca gtggatacca atcatgggga ccactctttg acaagttgtt ctttgccttc   3180
tgggtgattg ttcacttgta ccctttcctc aagggtttga tgggtcgaca gaaccggact   3240
cctaccattg ttgtggtctg gtctgttctc ttggcttcta tcttctcgtt gttgtgggtt   3300
aggattgatc ccttcactag ccgagtcact ggcccggaca ttctggaatg tggaatcaac   3360
tgttgagaag cgagcaaata tttacctgtt ttgagggtta aaaaaaacac agaatttaaa   3420
ttatttttca ttgttttatt tgttcacttt tttacttttg ttgtgtgtat ctgtctgttc   3480
gttcttctgt cttggtgtca taaatttatg tgtagaatat atcttactct agttactttg   3540
gaaagttata attaaagtga aag                                          3563
```

<210> SEQ ID NO 5
<211> LENGTH: 1065
<212> TYPE: PRT
<213> ORGANISM: Arabidopsis thaliana

<400> SEQUENCE: 5

```
Met Glu Ser Glu Gly Glu Thr Ala Gly Lys Pro Met Lys Asn Ile Val
1               5                   10                  15

Pro Gln Thr Cys Gln Ile Cys Ser Asp Asn Val Gly Lys Thr Val Asp
            20                  25                  30

Gly Asp Arg Phe Val Ala Cys Asp Ile Cys Ser Phe Pro Val Cys Arg
        35                  40                  45

Pro Cys Tyr Glu Tyr Glu Arg Lys Asp Gly Asn Gln Ser Cys Pro Gln
    50                  55                  60

Cys Lys Thr Arg Tyr Lys Arg Leu Lys Gly Ser Pro Ala Ile Pro Gly
65                  70                  75                  80

Asp Lys Asp Glu Asp Gly Leu Ala Asp Glu Gly Thr Val Glu Phe Asn
                85                  90                  95

Tyr Pro Gln Lys Glu Lys Ile Ser Glu Arg Met Leu Gly Trp His Leu
            100                 105                 110

Thr Arg Gly Lys Gly Glu Glu Met Gly Glu Pro Gln Tyr Asp Lys Glu
        115                 120                 125

Val Ser His Asn His Leu Pro Arg Leu Thr Ser Arg Gln Asp Thr Ser
    130                 135                 140

Gly Glu Phe Ser Ala Ala Ser Pro Glu Arg Leu Ser Val Ser Ser Thr
145                 150                 155                 160

Ile Ala Gly Gly Lys Arg Leu Pro Tyr Ser Ser Asp Val Asn Gln Ser
                165                 170                 175

Pro Asn Arg Arg Ile Val Asp Pro Val Gly Leu Gly Asn Val Ala Trp
            180                 185                 190

Lys Glu Arg Val Asp Gly Trp Lys Met Lys Gln Glu Lys Asn Thr Gly
        195                 200                 205

Pro Val Ser Thr Gln Ala Ala Ser Glu Arg Gly Gly Val Asp Ile Asp
    210                 215                 220

Ala Ser Thr Asp Ile Leu Ala Asp Glu Ala Leu Leu Asn Asp Glu Ala
225                 230                 235                 240

Arg Gln Pro Leu Ser Arg Lys Val Ser Ile Pro Ser Ser Arg Ile Asn
                245                 250                 255

Pro Tyr Arg Met Val Ile Met Leu Arg Leu Val Ile Leu Cys Leu Phe
```

-continued

```
                     260                 265                 270
Leu His Tyr Arg Ile Thr Asn Pro Val Pro Asn Ala Phe Ala Leu Trp
            275                 280                 285
Leu Val Ser Val Ile Cys Glu Ile Trp Phe Ala Leu Ser Trp Ile Leu
            290                 295                 300
Asp Gln Phe Pro Lys Trp Phe Pro Val Asn Arg Glu Thr Tyr Leu Asp
305                 310                 315                 320
Arg Leu Ala Leu Arg Tyr Asp Arg Glu Gly Glu Pro Ser Gln Leu Ala
                    325                 330                 335
Ala Val Asp Ile Phe Val Ser Thr Val Asp Pro Leu Lys Glu Pro Pro
            340                 345                 350
Leu Val Thr Ala Asn Thr Val Leu Ser Ile Leu Ala Val Asp Tyr Pro
            355                 360                 365
Val Asp Lys Val Ser Cys Tyr Val Ser Asp Asp Gly Ala Ala Met Leu
            370                 375                 380
Ser Phe Glu Ser Leu Ala Glu Thr Ser Glu Phe Ala Arg Lys Trp Val
385                 390                 395                 400
Pro Phe Cys Lys Lys Tyr Ser Ile Glu Pro Arg Ala Pro Glu Trp Tyr
                    405                 410                 415
Phe Ala Ala Lys Ile Asp Tyr Leu Lys Asp Lys Val Gln Thr Ser Phe
            420                 425                 430
Val Lys Asp Arg Arg Ala Met Lys Arg Glu Tyr Glu Glu Phe Lys Ile
            435                 440                 445
Arg Ile Asn Ala Leu Val Ser Lys Ala Leu Lys Cys Pro Glu Glu Gly
            450                 455                 460
Trp Val Met Gln Asp Gly Thr Pro Trp Pro Gly Asn Asn Thr Arg Asp
465                 470                 475                 480
His Pro Gly Met Ile Gln Val Phe Leu Gly Gln Asn Gly Gly Leu Asp
                    485                 490                 495
Ala Glu Gly Asn Glu Leu Pro Arg Leu Val Tyr Val Ser Arg Glu Lys
            500                 505                 510
Arg Pro Gly Phe Gln His His Lys Lys Ala Gly Ala Met Asn Ala Leu
            515                 520                 525
Val Arg Val Ser Ala Val Leu Thr Asn Gly Pro Phe Ile Leu Asn Leu
            530                 535                 540
Asp Cys Asp His Tyr Ile Asn Asn Ser Lys Ala Leu Arg Glu Ala Met
545                 550                 555                 560
Cys Phe Leu Met Asp Pro Asn Leu Gly Lys Gln Val Cys Tyr Val Gln
                    565                 570                 575
Phe Pro Gln Arg Phe Asp Gly Ile Asp Lys Asn Asp Arg Tyr Ala Asn
            580                 585                 590
Arg Asn Thr Val Phe Phe Asp Ile Asn Leu Arg Gly Leu Asp Gly Ile
            595                 600                 605
Gln Gly Pro Val Tyr Val Gly Thr Gly Cys Val Phe Asn Arg Thr Ala
            610                 615                 620
Leu Tyr Gly Tyr Glu Pro Pro Ile Lys Val Lys His Lys Lys Pro Ser
625                 630                 635                 640
Leu Leu Ser Lys Leu Cys Gly Gly Ser Arg Lys Lys Asn Ser Lys Ala
                    645                 650                 655
Lys Lys Glu Ser Asp Lys Lys Ser Gly Arg His Thr Asp Ser Thr
            660                 665                 670
Val Pro Val Phe Asn Leu Asp Asp Ile Glu Glu Gly Val Glu Gly Ala
            675                 680                 685
```

```
Gly Phe Asp Asp Glu Lys Ala Leu Leu Met Ser Gln Met Ser Leu Glu
    690                 695                 700
Lys Arg Phe Gly Gln Ser Ala Val Phe Val Ala Ser Thr Leu Met Glu
705                 710                 715                 720
Asn Gly Gly Val Pro Pro Ser Ala Thr Pro Glu Asn Leu Leu Lys Glu
                725                 730                 735
Ala Ile His Val Ile Ser Cys Gly Tyr Glu Asp Lys Ser Asp Trp Gly
            740                 745                 750
Met Glu Ile Gly Trp Ile Tyr Gly Ser Val Thr Glu Asp Ile Leu Thr
        755                 760                 765
Gly Phe Lys Met His Ala Arg Gly Trp Arg Ser Ile Tyr Cys Met Pro
770                 775                 780
Lys Leu Pro Ala Phe Lys Gly Ser Ala Pro Ile Asn Leu Ser Asp Arg
785                 790                 795                 800
Leu Asn Gln Val Leu Arg Trp Ala Leu Gly Ser Val Glu Ile Leu Phe
                805                 810                 815
Ser Arg His Cys Pro Ile Trp Tyr Gly Tyr Asn Gly Arg Leu Lys Phe
            820                 825                 830
Leu Glu Arg Phe Ala Tyr Val Asn Thr Thr Ile Tyr Pro Ile Thr Ser
        835                 840                 845
Ile Pro Leu Leu Met Tyr Cys Thr Leu Pro Ala Val Cys Leu Phe Thr
850                 855                 860
Asn Gln Phe Ile Ile Pro Gln Ile Ser Asn Ile Ala Ser Ile Trp Phe
865                 870                 875                 880
Leu Ser Leu Phe Leu Ser Ile Phe Ala Thr Gly Ile Leu Glu Met Arg
                885                 890                 895
Trp Ser Gly Val Gly Ile Asp Glu Trp Trp Arg Asn Glu Gln Phe Trp
            900                 905                 910
Val Ile Gly Gly Val Ser Ala His Leu Phe Ala Val Phe Gln Gly Ile
        915                 920                 925
Leu Lys Val Leu Ala Gly Ile Asp Thr Asn Phe Thr Val Thr Ser Lys
930                 935                 940
Ala Ser Asp Glu Asp Gly Asp Phe Ala Glu Leu Tyr Leu Phe Lys Trp
945                 950                 955                 960
Thr Thr Leu Leu Ile Pro Pro Thr Thr Leu Leu Ile Val Asn Leu Val
                965                 970                 975
Gly Val Val Ala Gly Val Ser Tyr Ala Ile Asn Ser Gly Tyr Gln Ser
            980                 985                 990
Trp Gly Pro Leu Phe Gly Lys Leu  Phe Phe Ala Phe Trp  Val Ile Val
        995                 1000                1005
His Leu  Tyr Pro Phe Leu Lys  Gly Leu Met Gly Arg  Gln Asn Arg
    1010                1015                1020
Thr Pro  Thr Ile Val Val  Trp Ser Val Leu Leu  Ala Ser Ile
    1025                1030                1035
Phe Ser  Leu Leu Trp Val Arg  Ile Asp Pro Phe Thr  Ser Arg Val
    1040                1045                1050
Thr Gly  Pro Asp Ile Leu Glu  Cys Gly Ile Asn Cys
    1055                1060                1065

<210> SEQ ID NO 6
<211> LENGTH: 3563
<212> TYPE: DNA
<213> ORGANISM: Artificial
<220> FEATURE:
```

<223> OTHER INFORMATION: ixr1-2 mutant variant

<400> SEQUENCE: 6

```
atcccaagat tctcctcttc gtcttcctta taaactatct ctctgtagag aagaaagctt      60
ggatccagat tgagagagat tcagagagcc acatcaccac actccatctt cagatctcat     120
gatttgaact attccgacgt ttcggtgttg aagcaacta agtgacaaat ggaatccgaa      180
ggggaaaccg cgggaaagcc gatgaagaac attgttccgc agacttgcca gatctgtagt    240
gacaatgttg gcaagactgt tgatggagat cgttttgtgg cttgtgatat ttgttcattc    300
ccagtttgtc ggccttgcta cgagtatgag aggaaagatg ggaatcaatc ttgtcctcag    360
tgcaaaacca gatacaagag gctcaaaggt agtcctgcta ttcctggtga taaagacgag    420
gatggcttag ctgatgaagg tactgttgag ttcaactacc ctcagaagga gaaaatttca    480
gagcggatgc ttggttggca tcttactcgt gggaagggag aggaaatggg ggaaccccag    540
tatgataaag aggtctctca caatcatctt cctcgtctca cgagcagaca agatacttca    600
ggagagtttt ctgctgcctc acctgaacgc ctctctgtat cttctactat cgctggggga    660
aagcgccttc cctattcatc agatgtcaat caatcaccaa atagaaggat tgtggatcct    720
gttggactcg ggaatgtagc ttggaaggag agagttgatg gctggaaaat gaagcaagag    780
aagaatactg tcctgtcag cacgcaggct gcttctgaaa gaggtggagt agatattgat     840
gccagcacag atatcctagc agatgaggct ctgctgaatg acgaagcgag gcagcctctg    900
tcaaggaaag tttcaattcc ttcatcacgg atcaatcctt acagaatggt tattatgctg    960
cggcttgtta tcctttgtct cttcttgcat taccgtataa caaacccagt gccaaatgcc   1020
tttgctctat ggctggtctc tgtgatatgt gagatctggt ttgccttatc ctggattttg   1080
gatcagtttc ccaagtggtt tcctgtgaac cgtgaaacct acctcgacag gcttgcttta   1140
agatatgatc gtgaaggtga gccatcacag ttagctgctg ttgacatttt cgtgagtact   1200
gttgacccct tgaaggagcc acccttgtg acagccaaca cagtgctctc tattctggct    1260
gttgactacc cagttgacaa ggtgtcctgt tatgttttg atgatggtgc tgctatgtta    1320
tcatttgaat cacttgcaga acatcagag tttgctcgta atgggtacc attttgcaag     1380
aaatatagca tagagcctcg tgcaccagaa tggtactttg ctgcgaaaat agattacttg   1440
aaggataaag ttcagacatc atttgtcaaa gatcgtagag ctatgaagag ggaatatgag   1500
gaatttaaaa tccgaatcaa tgcacttgtt tccaaagccc taaatgtcc tgaagaaggg    1560
tgggttatgc aagatggcac accgtggcct ggaataata cagggaccaa tccaggaatg    1620
atccaggtct tcttagggca aaatggtgga cttgatgcag agggcaatga gctcccgcgt   1680
ttggtatatg tttctcgaga aaagcgacca ggattccagc accacaaaaa ggctggtgct   1740
atgaatgcac tggtgagagt ttcagcagtt cttaccaatg gacctttcat cttgaatctt   1800
gattgtgatc attacataaa taacagcaaa gccttaagaa agcaatgtg cttcctgatg    1860
gacccaaaac ccgggaagca agtttgttat gttcagttcc cacaaagatt tgatggtatc   1920
gataagaacg atagatatgc taatcgtaat accgtgttct ttgatattaa cttgagaggt   1980
ttagatggga ttcaaggacc tgtatatgtc ggaactggat gtgttttcaa cagaacagca   2040
ttatacggtt atgaacctcc aataaaagta aaacacaaga agccaagtct tttatctaag   2100
ctctgtggtg gatcaagaaa gaagaattcc aaagctaaga aagagtcgga caaaaagaaa   2160
tcaggcaggc atactgactc aactgttcct gtattcaacc tcgatgacat agaagaggga   2220
gttgaaggtg ctggttttga tgatgaaaag gcgctcttaa tgtcgcaaat gagcctggag   2280
```

```
aagcgatttg  acagtctgc  tgttttttgtt  gcttctaccc  taatggaaaa  tggtggtgtt      2340
cctccttcag  caactccaga  aaaccttctc  aaagaggcta  tccatgtcat  tagttgtggt      2400
tatgaggata  agtcagattg  gggaatggag  attggatgga  tctatggttc  tgtgacagaa      2460
gatattctga  ctgggttcaa  aatgcatgcc  cgtggatggc  gatccattta  ctgcatgcct      2520
aagcttccag  ctttcaaggg  ttctgctcct  atcaatcttt  cagatcgtct  gaaccaagtg      2580
ctgaggtggg  ctttaggttc  agttgagatt  ctcttcagtc  ggcattgtcc  tatatggtat      2640
ggttacaatg  ggaggctaaa  atttcttgag  aggtttgcgt  atgtgaacac  caccatctac      2700
cctatcacct  ccattcctct  tctcatgtat  tgtacattgc  tagccgtttg  tctcttcacc      2760
aaccagttta  ttattcctca  gattagtaac  attgcaagta  tatggtttct  gtctctcttt      2820
ctctccattt  tcgccacggg  tatactagaa  atgaggtgga  gtggcgtagg  catagacgaa      2880
tggtggagaa  acgagcagtt  ttgggtcatt  ggtggagtat  ccgctcattt  attcgctgtg      2940
tttcaaggta  tcctcaaagt  ccttgccggt  attgacacaa  acttcacagt  tatttcaaaa      3000
gcttcagatg  aagacggaga  ctttgctgag  ctctacttgt  tcaaatggac  aacacttctg      3060
attccgccaa  cgacgctgct  cattgtaaac  ttagtgggag  ttgttgcagg  agtctcttat      3120
gctatcaaca  gtggataccca  atcatgggga  ccactctttg  gtaagttgtt  ctttgccttc      3180
tgggtgattg  ttcacttgta  cccttttcctc  aagggtttga  tgggtcgaca  gaaccggact      3240
cctaccattg  ttgtggtctg  gtctgttctc  ttggcttcta  tcttctcgtt  gttgtgggtt      3300
aggattgatc  ccttcactag  ccgagtcact  ggcccggaca  ttctggaatg  tggaatcaac      3360
tgttgagaag  cgagcaaata  tttacctgtt  ttgagggtta  aaaaaaacac  agaatttaaa      3420
ttatttttca  ttgttttatt  tgttcacttt  tttacttttg  ttgtgtgtat  ctgtctgttc      3480
gttcttctgt  cttggtgtca  taaatttatg  tgtagaatat  atcttactct  agttactttg      3540
gaaagttata  attaaagtga  aag                                                3563
```

<210> SEQ ID NO 7
<211> LENGTH: 19
<212> TYPE: DNA
<213> ORGANISM: Artificial
<220> FEATURE:
<223> OTHER INFORMATION: Primer Sequence

<400> SEQUENCE: 7

```
cgaacttgag acctcttga                                                          19
```

<210> SEQ ID NO 8
<211> LENGTH: 19
<212> TYPE: DNA
<213> ORGANISM: Artificial
<220> FEATURE:
<223> OTHER INFORMATION: Primer Sequence

<400> SEQUENCE: 8

```
gcttacctgg agacagtca                                                          19
```

<210> SEQ ID NO 9
<211> LENGTH: 19
<212> TYPE: DNA
<213> ORGANISM: Artificial
<220> FEATURE:
<223> OTHER INFORMATION: Primer Sequence

<400> SEQUENCE: 9
catgatccat cgtcttagt                                                19

<210> SEQ ID NO 10
<211> LENGTH: 18
<212> TYPE: DNA
<213> ORGANISM: Artificial
<220> FEATURE:
<223> OTHER INFORMATION: Primer Sequence

<400> SEQUENCE: 10
aatatcgctt gttttgc                                                  18

<210> SEQ ID NO 11
<211> LENGTH: 19
<212> TYPE: DNA
<213> ORGANISM: Artificial
<220> FEATURE:
<223> OTHER INFORMATION: Primer Sequence

<400> SEQUENCE: 11
tccaaagcta aatcgctat                                                19

<210> SEQ ID NO 12
<211> LENGTH: 19
<212> TYPE: DNA
<213> ORGANISM: Artificial
<220> FEATURE:
<223> OTHER INFORMATION: Primer Sequence

<400> SEQUENCE: 12
ctccgtctat tcaagatgc                                                19

<210> SEQ ID NO 13
<211> LENGTH: 19
<212> TYPE: DNA
<213> ORGANISM: Artificial
<220> FEATURE:
<223> OTHER INFORMATION: Primer Sequence

<400> SEQUENCE: 13
acctgaacca tcctccgtc                                                19

<210> SEQ ID NO 14
<211> LENGTH: 19
<212> TYPE: DNA
<213> ORGANISM: Artificial
<220> FEATURE:
<223> OTHER INFORMATION: Primer Sequence

<400> SEQUENCE: 14
tcattttggc cgacttagc                                                19

<210> SEQ ID NO 15
<211> LENGTH: 22
<212> TYPE: DNA
<213> ORGANISM: Artificial
<220> FEATURE:
<223> OTHER INFORMATION: Primer Sequence

<400> SEQUENCE: 15
tctccccact agttttgtgt cc                                            22

<210> SEQ ID NO 16
<211> LENGTH: 21
<212> TYPE: DNA
<213> ORGANISM: Artificial

```
<220> FEATURE:
<223> OTHER INFORMATION: Primer Sequence

<400> SEQUENCE: 16
gaaatccaaa tcccagagag g                                              21

<210> SEQ ID NO 17
<211> LENGTH: 18
<212> TYPE: DNA
<213> ORGANISM: Artificial
<220> FEATURE:
<223> OTHER INFORMATION: Primer Sequence

<400> SEQUENCE: 17
gatttcccca gacgattt                                                  18

<210> SEQ ID NO 18
<211> LENGTH: 19
<212> TYPE: DNA
<213> ORGANISM: Artificial
<220> FEATURE:
<223> OTHER INFORMATION: Primer Sequence

<400> SEQUENCE: 18
tcattttggc cgacttagc                                                 19

<210> SEQ ID NO 19
<211> LENGTH: 24
<212> TYPE: DNA
<213> ORGANISM: Artificial
<220> FEATURE:
<223> OTHER INFORMATION: Primer Sequence

<400> SEQUENCE: 19
cagttaatga aacaagcttt gttc                                           24

<210> SEQ ID NO 20
<211> LENGTH: 21
<212> TYPE: DNA
<213> ORGANISM: Artificial
<220> FEATURE:
<223> OTHER INFORMATION: Primer Sequence

<400> SEQUENCE: 20
gttgagaaaa tcactttggt g                                              21

<210> SEQ ID NO 21
<211> LENGTH: 17
<212> TYPE: DNA
<213> ORGANISM: Artificial
<220> FEATURE:
<223> OTHER INFORMATION: Primer Sequence

<400> SEQUENCE: 21
tggttagatt tgctgtt                                                   17

<210> SEQ ID NO 22
<211> LENGTH: 20
<212> TYPE: DNA
<213> ORGANISM: Artificial
<220> FEATURE:
<223> OTHER INFORMATION: Primer Sequence

<400> SEQUENCE: 22
attctgcatt attagttgtc                                                20
```

<210> SEQ ID NO 23
<211> LENGTH: 29292
<212> TYPE: DNA
<213> ORGANISM: Arabidopsis thaliana

<400> SEQUENCE: 23

| | | | | | |
|---|---|---|---|---|---|
| agcagcatta | ggaaataaat | atctcttctt | cagagcttct | cattaaagtc | cgtataacta | 60 |
| actaaacact | cttagtagaa | tttacttttg | acattttcca | acgtaaaaaa | gatttatgac | 120 |
| ccaaaaaaaa | aaaaaagagt | ttgaccttgt | aatcacttaa | cttgtgtcgt | cgttcaagta | 180 |
| caacgcatgt | gtgaggaaaa | aaagaataat | gtgttttat | aataataatg | aaaagccaaa | 240 |
| acagaccgat | caggtcaaaa | gaaagccgta | agaaaatcc | aacttaaaat | aaaaataaaa | 300 |
| tctcttttac | caaacagata | tacagagaga | cttcaatcag | aggaaataaa | taaatttcat | 360 |
| tatttctctt | tctgaattaa | taaaaaggtt | tcttgttgaa | ttgaatttgt | agctgtgttt | 420 |
| aacgtagtag | cacttgggtt | ttagatagac | aacgtaacca | aaactgtttc | atgttctgtc | 480 |
| tgtattctct | cttttgcttt | tttgggtttc | ctccttcttt | ctcatctttg | ctgcggtgca | 540 |
| ttttttttctc | gggaaaatcc | tttctgggct | tccgggaaa | gttttcttgt | cagattcgga | 600 |
| aaggtaccaa | aaaaaataaa | ttaataaaaa | cttaccaaac | agattttgtg | tttatctctc | 660 |
| tctctataga | ttcttttgat | cacaaatcct | tttcgttttt | gatcatattt | tgattgagaa | 720 |
| caaaacaatc | ttcaaagtct | caaccttta | gtttgattga | tcttttttttg | gtaagtaaat | 780 |
| cttctgtcgt | agattcgata | ttttctgatc | ttctcttttc | gaattcttca | atcttcaacg | 840 |
| atcccaatct | tcttcttctg | gaaatctatt | ttgcttcttc | ttcaaatttt | ctggggaaaa | 900 |
| aatcaaattc | ttgagttaat | tagactccga | ttttgttgaa | tcgagaaacg | atgaaagcat | 960 |
| cgggttcatt | agatagctgg | agagaatatt | tccgacggcg | aggagattcc | gatatattcg | 1020 |
| ggatcatcga | tcatgcgatc | atggtggctg | ctactgattg | tcctaacaaa | ttcaaatcca | 1080 |
| gaagagacaa | aatcgccgag | cttttattct | cctgtagagt | gaatcgttgc | gtcggatgcg | 1140 |
| accatcttga | attgtctgtt | cccggagacg | acgaggctaa | ccgtggaacc | accggaaatg | 1200 |
| gtggtggtgg | tacggcggtt | gatgaagatt | atgaggttgc | tggtggtagt | aaagagagca | 1260 |
| aagctaatag | tagcagaggg | gataataatc | agattgttag | caattataca | tttgatgaag | 1320 |
| ctgaggcttt | gagtgatgag | attgaagagt | tttctgtggt | ttctaaggag | gttgctagga | 1380 |
| tcaaagagat | cttgctcaac | aaagaagatg | aggtttgatt | ctcaagttct | tgaaatttca | 1440 |
| tcaatgtgaa | gatttttttt | ttgtgttttc | tgattggttc | ttttttgtat | tctcttgcag | 1500 |
| ccaaactcgg | tgttactcga | ttcttttaaga | catcttaagt | tgatgtcttt | gaatgtggat | 1560 |
| attcttaagg | ttggttatct | tggtggatag | tgtatgaagt | tgttgttgat | gatccttgag | 1620 |
| attcttaagg | tttgcggtta | ttctcgcaga | gtactgagat | tggaaaggct | gttaatggcc | 1680 |
| tcaggaaaca | ttcttctgat | aagattcgac | aactcgctaa | gactcttatc | gcgtatgagt | 1740 |
| ttttgatctt | tcacaagttt | gattgacatt | tgctatgctt | ttgcacttttt | gaatctcaca | 1800 |
| tttgagtttt | tgatatgttt | atgcagagaa | tggaaggagt | tggtggatca | atgggtgaat | 1860 |
| accacaaagg | aaatcactgg | taattgcgct | ttctctgtct | cgcttttcga | tcttttatga | 1920 |
| ctggcttcgt | gtcttaccgt | ttggtttctt | gaattagatc | catagtctttt | ggttctaatt | 1980 |
| ttgtgtttaa | aacaggtgct | gaaggtacac | cagagtctgc | aaacccgtct | gtccttgatg | 2040 |
| aagaagaggc | gtttccatcg | cttccatatg | atgttgatat | ctttacacct | gaaccaaacg | 2100 |
| gatttgaaat | ctcacacttc | tttgattcct | tggactttga | tggaagtgag | ttttaaaact | 2160 |

-continued

```
atgtcttgtt tgtttgagaa catgttctta gctacgtgtt gattgatttt cttggggatg    2220
tttgtttcag atcctcgtaa ctctgaagaa cacaacacaa gccgagagca tgaaagaagg    2280
ccacaaaata tcgccaagag aaaacctgag ggaacacaaa tgaggataca agatgctcct    2340
tttagatcta ttaagccatc atcagctact gattttgatg ggactagaag acctgtaaag    2400
caaagtacag agcaaaggat gaagaacgaa acggtatctg ttcacaagtc tgaaaaaccc    2460
atgatccaaa ggaaaccggt tgttacagaa cagaagcgga aagctcctgg acctcaacaa    2520
gaagtgagtg tggagacaaa gctcttgtct aatatcctat tcttggacgt agaattgatg    2580 gtgttttttgc tcttgtccct tgcagaaact taaaggtctt gatgcagacg caaagtttga    2640
gtttgcaaag aggaaacttc aagaaagcta ccagcatcac gagaatggtt cgtttcattt    2700
ccttttcttt gtttcgagtt ttttgttaca ttcttgaaaa caaagaact taaaaatgtt    2760 tgtgatcttg ccacagccaa gaagcagcga acgatacaag tacttgagat gatcccaaag    2820
caaggtagtg ctcagaaacc gcaactcaag agacctggaa tgagcaacag gaattgggct    2880
aatgggagaa aatagtttct gctttgttca aatggtgaat aattctcggc aaaagatatt    2940
actccatact taccacacat atctcgcaat ctctggtgca ataaaggtaa acagagtcta    3000
gttccacaaa gctggagaca gaaacaagca gaggagaagg aacagaatcc aacataactt    3060
tactttgaac aaactgttta ctcctctgtt ttgttctgtc ttggattcac caattgcagc    3120
aagataggga taccaattat tgtttctttt atgtgttctt tactacattc ttgagacttt    3180
cggtacagtc ccggtttagt cgggttatgt tcggttttgg gacaaggaga gaggtccctt    3240
ttacatatat atcatataaa aatagtaaaa gagagggtag aaaagctcat tcgaaattga    3300
ccggctcttc acctaacttt gtatagtaat gtgaaatgat ttgggacaca atatagagat    3360
gatgacactt ttttccaaat aaataaatat ttatataatg atatccaatt gttatgaatg    3420
aatgtgattg tgaccgaatg ttgtcatttc ttattactta tgtatataaa ataagatggc    3480
attggaaagg cttaaggaag gtgggtggat aagaaaagag gagaaggtag tgggggggtgg    3540 gagataacgt ggatggatag gaatgttgtt gcagtgtggt cttttgtgcgt gttggtattt    3600 tttattcaat gttgttatta tctcggcgtt acgcgttcac gcatttcacc acatgaacca    3660
cgtggacttc tacaacttct attaatcttt cactccattt ctattgaaag aaaaacagtt    3720
ggatagagat aaatctagtt ttatggtcac gatttatttt cgtgaaaagg aaaatgcact    3780
ttttagtttg attaaataag tacacccaaa cacttttgga caaaaacaaa cgtaatgatt    3840
tttggcgtga tggtaaattc gtatggatgt gttggttatt tttgtaaact ttagcatgtg    3900
agagaaaaaa aaagttgagc atgtgaaaat acaaaaaata ttgttgtctg tgtacaaaaa    3960
ctgaaatgac atttaacatt tagtaagttt caaaatttaa aacattaact cataatctca    4020
aaactttaaa ctaaacaaaa aactgcaatt ccaaaagctc tagaacttaa atcttactat    4080
tgatgcagcg aaatgtcttt agttttttttt tttttaacaa aattatgaga tctttttttg    4140
ttgttggaaa tatcactaca aaatgtctaa ttcatactat tttaagaata taaaaaatct    4200
catttataat caatatgcaa tgaataaatt gacctatatc cattacatac tttgttagat    4260
tacacttcat ttttgatgtg aaacattcta gcaggattaa tgactcaata aaaatagaaa    4320
aatatgcact taattaatt aatgatattt ggttcccagt cgttggaatt gggaagactt    4380
gaaaagtagt gaagcatgtg aaaaaatgct aatatataga tccgagagat tgtgactatt    4440
tcattaattg accctaaaga agaaggcatc ttttttccat gcagagaatc gacatgtttt    4500
```

-continued

```
tggagagaag ttgacatgga caaaaaaaca acaatagcat cagttctgct gccgacacaa    4560
agtatttagg ttaccatttt ataatttatg tggagtttta gatagataga cagctaatcg    4620
ttacaaaatt ccttgcgtcg caatcaacgg tgagataaag aaataagagt tgacaaatga    4680
aataagggaa aatagttgag tatcggttct aaacaaaaaa aaatccatca tttagaacgt    4740
tcatcaaatt ttcatggttt tgaaaattga ttatactata taatcgaata actcaacttg    4800
tttaatttga gtattgttga gtcttatttg atttacgatt ggacaaagtc tggaaacatt    4860
atcagaatta tgcgcaattt aaacctttct cataaataaa tgaaatttga aagaattgag    4920
ttcattgttg gatagtctta ggttttgatt aaaaataatt caccattgtg tttcgttagg    4980
ttgaagtaat catttataac gtaaattaaa gtatcattac atgggataag aatcattatt    5040
tatatacgat tacgaattag aattgaaatt cagaaaatgg ttttatataa gcttttgag     5100 ataaataaaa tacattaaca aataatataa ttataaaata tcaatgcata taattgtatt    5160
ttattgatct caaatacttt gataaataaa tacataaagg ttttccaat cggttcttag    5220 ggggatcaat tcctagttta ttaaaaatca acatagttct tcacaagaaa tatagaacaa    5280
gaaagttttg ttcagaaaaa aacaaaaaaa caaaagaaa gaaaaggggt agtacaaagt     5340
tttaatcggt gaagactaat tattagaaga agaagaacaa gaaggaaatt attccaaaaa    5400
aaagaagaac aagaaggaaa tgtgttgtgt tttgttgatc acaccccacc aaccattgtg    5460
ttgcccgtct cttgtaagga gaagaagtat tgtgttcca attccaccat ctgccctcca     5520
tctgcatgat caaatttgca cctccggaaa cttcacattt tccggggatg attccgacaa    5580
ttagatgagg aaaacaagca gactccaaga aagagccaaa gtagagccac gtcacagaaa    5640
ccaaagagaa aaaagcttac cttccatcga tgcctacgag aagaacagtg ttctctgatc    5700
caaaacctac aatgaacttg gtggaagctg gcaacgagaa ctgagcaaac gaccgttcat    5760
tttcgtacaa atactttggt aagatcactc ttatgaatga cgacgatgaa gccggatcaa    5820
aactaagaat gtcaggtctc aaacgaaata catggagagt ccctttttca cttgacgcag    5880
cgacccattt cagattcgaa gagattgcaa cgttatagat ctctgctctt tccactcctc    5940
tccgaaactt caccaagaaa accaaacata tcaaaatact aagtaattaa caaaccataa    6000
tcacaaaaaa aaaccacaa aattttagct agggtttata acaaaaacaa aaaaaggtta    6060
gggctaatta cctcttgtaa gagagtacca tcaacggcgt taaagatcct gatcaaagtt    6120
cctttggtgc tagcggttgc gaggagactt ccatcgagag tcaaagtcat gcaagctata    6180
gcagaatcat gtgctttgat gaatttgata acattccatc tcaagtcatg gacctgaact    6240
tgtcccggat gaaacccggg acaagccaag actgctttcg actcaacgtg agtgacgcaa    6300
cacagtcctt tcgggttcat gagggtttcg atcacacggt caaccttaag gttgttgaaa    6360
gtgtagacat agatgttttg tttcaggacc accacaacgt gttctctcgc tagtttcaca    6420
gcgataactt ctgatttaaa agtgagctcg ctgaggcagc aatttcggta atcatcccaa    6480
acgaatactt tgttaggagg gtactcggaa ttgttataac cattgccaac aaaagcgaat    6540
aagttagaaa ggaagagcat ctcagcaact ttgaagcctg attcgtgcgg ggcacggctg    6600
atgcttttct ttatcattgg tttgcagcta tatacattga aaccgtgatt tgttccaacg    6660
atgaaaccac tgcatacctg gttccaagct actgataaca ccttcaagtc acttttgct     6720 tcatcacgtg gtgaatcgaa agtttcagat cttgaaagcg ttaagattcc acggacagtg    6780
gagacaatcg aattcattct tctcttttcc aaaccaaatt cacagaagaa aaaccgaaga    6840
gacaatactt tagaatatca aacgcttctc atgaaaagtc gttgggaaat tgatgtttat    6900
```

```
cgtttggtaa tttatacaca ggtaacaaaa tcctaaatag agtgcgaata ggaaaagact   6960
tcaaaccata tatatcacat ctttaatata atacgtttat gaaaattaaa taaaaatcaa   7020
acctagaaaa tctcattaca aaactccacg tcttcatcta actataattg tgtttatcta   7080
tttaattttg tttaaaaagg atttcattaa atctaaatgg atacaaagtt ttcggtcaaa   7140
aaaaaactag acctaattac aaattataga tatagattga acttaaccta ctcatggctg   7200
acttgaaacg aatgtggaat gtgactgatc cttgtaatca aacttgtaga atctctgaag   7260
cttttagcgg caaccaatga ctcatcgatg agacattgtt gcgaaaaggt atatcgatct   7320
tcttaaagat ttgagctgtg tcgagactcc gcaaaagtgt gagtttctat ctagagctcc   7380
tatatagtcg cttcccaagc aatggtccat ggataattca aaatttaaca atcttcccgg   7440
ggtaataatg aggtgttttc cttttacttt ttttgctact acctttttttt cccctccttt   7500 tgttgtaaca ttcaatattg gattaagcaa gtccttaagt ttcggaactg aagatgtgtt   7560
ttgtcataga tctagagatt tgagggagac aggtttggca ttgatggatg ctgcaaaatc   7620
attgtgttaa ctgtaacaaa agaacccaat catgagtctt tgaggcacag gtgaaaaatc   7680
atcaaaaatc atattactaa tgtcacttca tagtcaatct tcatggatta ataatccatc   7740
attattcatt tagttagacc aaaccaacct aatgaattgg agagacttga aaagcaaaac   7800
tcatagtaca gcaacacagt gttatatcct cacaagtcaa tctttgattc tctcttgtgt   7860
tcttcaactt taagcaccta attctgttaa atgcaattta tcagatttaa acagaggacc   7920
ccacttgcag tggttggtta ggtaaataat ctctccatac aaaattcaca ctttactctt   7980
ttagtggtta aaaaaagtct tgccaatgag tctcttcgaa acacaacata acttttatat   8040
caattttggt gtgtccaaat atatgcacca atgcaggatc ggattctgtc aatatgacca   8100
ataaaatgac aacacgagac agatcatttg gttatttttt tctgttaatt ttgatacatt   8160
attgttgaat tacttgaaga aatcgatcac tacctttttc cttgatttgc atgctgtata   8220
atgcaaagaa aagaaaaagc aaaatattcc tttaatctgt agtgtgtttt gtctcttaaa   8280
gaacaaatga aagaagcaaa aaatgggatg cttttgcttt cttttcccctcc tttcttttacg   8340 gtgtcttgct ttttattttc ctttacatag ttatttgaat ttgaatccac tttttgttat   8400
attaaaaaca acccattatg tttacttaac aatggattca aaccaactaa tcattgttttt   8460 ttatcttatt tgagctcacc tcttcttttt gactctcttt acccacatga aaacaaacac   8520
taagaacaaa acttcatag gaaactcaat tttctctctt tctcagatca tggtgtgagt   8580
caccaaatag ctcaaccatg aattcttctc acactgcctt cgttgctgct tccttcttct   8640
tcctcttact cgccgcaacc gcggttttgg tttcagccga tttagcatca gacgaacaag   8700
cccttctcaa cttttgcagca tcagtcccac atccaccaaa actcaactgg aacaagaacc   8760
tctctctctg ctcttcatgg atcggcatta cttgtgatga atccaaccc accagccgcg   8820 ttgtagctgt ccgtcttcca ggagttggcc tctacggctc aatccctcct gccacattag   8880
gcaaactaga cgctctcaaa gtccttagcc tcagatccaa ctctctcttt ggaactttac   8940
cttctgatat tctctcactc ccttctcttg aataccttta tctccaacac aacaacttct   9000
ccggcgaact caccactaat tctttgccgt cgatctccaa gcagcttgtt gtcttggact   9060
tgtcttataa ctctttatct ggtaacattc cttccggtct ccggaacttg tctcagatca   9120
ctgtattgta ccttcaaaac aactcttttg atggtcccat tgattctctt gatctcccga   9180
gtgtaaaagt tgtaaatttg agctataaca acttaagtgg acccatccct gagcatctca   9240
```

-continued

| | | | | |
|---|---|---|---|---|
| agaagtcacc | ggaatattct | ttcatcggaa | actcattact | atgtggtcca cctctgaatg | 9300 |
| catgttccgg | aggagccatc | tctccgtctt | caaatttgcc | tagaccgttg acagagaatc | 9360 |
| tccatcctgt | ccggaggaga | cagagtaaag | cttatataat | cgccattgta gtcggatgct | 9420 |
| ctgtggccgt | tcttttcctt | gggattgttt | tcttggtttg | tctggtgaag aagacgaaga | 9480 |
| aagaagaagg | aggcggtgaa | ggagtgcgaa | cgcagatggg | gggagtgaat agcaagaaac | 9540 |
| cgcaggattt | cggagcgga | gttcaagatc | cagagaagaa | caagctcttc ttcttcgaaa | 9600 |
| gatgcaatca | taatttcgat | cttgaggatc | tcttgaaagc | ttctgctgaa gttcttggta | 9660 |
| aagggagttt | cggaacggcc | tacaaggccg | tgcttgagga | cacaaccgca gtggtggtga | 9720 |
| aacgtttaag | agaagtcgtg | gcgagcaaga | aagagtttga | acagcaaatg gagatagttg | 9780 |
| ggaagattaa | ccagcattct | aatttcgtac | cactcctcgc | ttattactat tcgaaagacg | 9840 |
| agaagctatt | ggtctacaag | tacatgacga | aggaagctt | gttcgggatc atgcacggtg | 9900 |
| agtcataaag | agaccaaacc | ctaacttttt | tggtaatgta | aagcttgtgt gtgggtcacg | 9960 |
| aaaaattgtt | ccttttgga | tttttggac | aggaaacaga | ggagacagag gagtcgactg | 10020 |
| ggaaacgcgg | atgaagatcg | cgacagggac | ttcaaaagca | atctcttacc ttcactcctt | 10080 |
| aaaattcgtt | cacggagaca | tcaaatcatc | aaacatactt | ctcactgaag accttgagcc | 10140 |
| atgtctgtcc | gacacatctt | tagtcactct | cttcaacctt | ccaactcaca caccgcgaac | 10200 |
| cattggctac | aatgctcctg | aagttattga | gacgaggaga | gtcagtcaaa gatcagacgt | 10260 |
| ttatagcttt | ggtgtggtga | ttctcgaaat | gctaaccggg | aagacaccct taactcagcc | 10320 |
| tggtctcgag | gatgagcgtg | tcgtcattga | tcttccgaga | tgggttcggt ctgttgtgag | 10380 |
| agaagagtgg | actgcagagg | ttttcgatgt | ggagctcttg | aagtttcaga acattgaaga | 10440 |
| ggagatggtt | cagatgcttc | agctagcgtt | ggcctgtgtt | gcaaggaatc cagaatcgag | 10500 |
| gccaaagatg | gaagaggtcg | cgaggatgat | tgaagatgtg | aggagattgg atcagtctca | 10560 |
| gcagttacag | caaaacagaa | catcctcaga | ggctacttcc | aatgtctctg aatgattcct | 10620 |
| cattccgacc | aaaagtttct | ttgatcaatt | ctacttctat | cttattactt ttgaatccca | 10680 |
| gttaaaaata | atttctcttt | gcatcgtagt | ttagtgctta | tgatcaaacg taactgcttt | 10740 |
| cactaatgaa | aattgaaaaa | tcataaccac | tgctttaact | acagaaacaa aaaaatattc | 10800 |
| gctttcactt | taattataac | tttccaaagt | aactagagta | agatatattc tacacataaa | 10860 |
| tttatgacac | caagacagaa | gaacgaacag | acagatacac | acaacaaaag taaaaaagtg | 10920 |
| aacaaataaa | acaatgaaaa | ataatttaaa | ttctgtgttt | tttttaaccc tcaaaacagg | 10980 |
| taaatatttg | ctcgcttctc | aacagttgat | tccacattcc | agaatgtccg ggccagtgac | 11040 |
| tcggctagtg | aagggatcaa | tcctaaccca | caacaacgag | aagatagaag ccaagagaac | 11100 |
| agaccagacc | acaacaatgg | taggagtccg | gttctgtcga | cccatcaaac ccttgaggaa | 11160 |
| agggtacaag | tgaacaatca | cccagaaggc | aaagaacaac | ttaccaaaga gtggtcccca | 11220 |
| tgattggtat | ccactgttga | tagcataaga | gactcctgca | acaactccca ctaagtttac | 11280 |
| aatgagcagc | gtcgttggcg | gaatcagaag | tgttgtccat | ttgaacaagt agagctcagc | 11340 |
| aaagtctccg | tcttcatctg | aagcttttga | ggtaactgtg | aagtttgtgt caataccggc | 11400 |
| aaggactttg | aggatacctt | gaaacacagc | gaataaatga | gcggatactc caccaatgac | 11460 |
| ccaaaactgc | tcgtttctcc | accattcgtc | tatgcctacg | ccactccacc tcatttctag | 11520 |
| tatacccgtg | gcgaaaatgg | agagaaagag | agacagaaac | catatacttg caatgttact | 11580 |
| aatctgcaaa | agaggaacaa | tagaaccagc | tgatcaggat | ttggaaccgt aaatagatga | 11640 |

```
caaacacaac atggtttcag ttaaacagaa cgtaattaag gtttgttcta gagatagaga   11700
tagagataga gatagataga cagagagagg tgtcaaacct gaggaataat aaactggttg   11760
gtgaagagac aaacggctgg caatgtacaa tacatgagaa gaggaatgga ggtgataggg   11820
tagatggtgg tgttcacata cgcaaacctc tcaagaaatt ttagcctccc attgtaacca   11880
taccatatag gacaatgccg actgaagaga atctcaactg aacctaaagc ccacctcagc   11940
acttggttca gacgatctga aagattgata ggagcagaac ccttgaaagc tggaagctta   12000
ggcatgcagt aaatggatcg ccatccacgg gcatgcattt tgaacccagt cagaatatct   12060
tctgtcacag aaccatagat ccatccaatc tgaagaaaga cagcggaaaa tataaacaaa   12120
gtgaatgcca aagtggatat gtcagaacaa tgcagattca tgtaggagtt caaatgagat   12180
tatacctcca ttccccaatc tgacttatcc tcataaccac aactaatgac atggatagcc   12240
tctttgagaa ggttttctgg agttgctgaa ggaggaacac caccattttc cattagggta   12300
gaagcaacaa aaacagcaga ctgtccaaat cgcttctcca ggctcatttg cgacattaag   12360
agcgcctttt catcatcaaa accagcacct aagtttcaca aatgccaaat agttaagaca   12420
tgatgagata cctagtatgg aaactattta gacaactgtc aactataaat aatccctcc   12480 cctggatcaa tatttcaaac agcaacatat gggtataacg gaaaccaaag aagaaataaa   12540
aacagttgta ccttcaactc cctcttctat gtcatcgagg ttgaatacag gaacagttga   12600
gtcagtatgc ctgcctgatt tcttttttgtc cgactctttc ttagctttgg aattcttctt   12660
tcttgatcca ccacagagct tagataaaag acttggcttc ttgtgtttta cttttattgg   12720
aggttcataa ccgtataatg ctgttctgtt gaaaacacat ccagttccga catatacagg   12780
tccttgaatc ccatctaaac ctctcaagtt aatctggaaa acatatcatg gaaaaattac   12840
gacaaactca agaaactgtg agtttaatgt atattcgtgt ctaaaagcaa tttgaaagaa   12900
caagaaaatt agacgcaagt ataggtaagt gtgacttaca tcaaagaaca cggtattacg   12960
attagcatat ctatcgttct tatcgatacc atcaaatctt tgtgggaact gaacataaca   13020
aacttgcttc ccgaggtttg ggtccatcag gaagcacatt gcttctctta aggctttgct   13080
gttatttatg taatgatcac aatcaagatt caagatgaaa ggtccattgg taagaactgc   13140
tgaaactctc acctattcat ttgaaaagta cccagattag actaacaaat tggtcagaat   13200
gaagaagtca aaaatccaag atcagaaact taccagtgca ttcatagcac cagccttttt   13260
gtggtgctgg aatcctggtc gcttttctcg agaaacatat accaaacgcg ggagctcatt   13320
gccctctgca tcaagtccac cattttgccc taagaagacc tgcattcagc aaatggtact   13380
tcaataatga acttctagag agaaagagag agcattctcg attccatagt taaaaccaat   13440
ttcttacctg gatcattcct ggatggtccc ttgtattatt tccaggccac ggtgtgccat   13500
cttgcataac ccaccctttct tcaggacatt ttagggcttt ggaaacaagt gcattgattc   13560
ggattttaaa ttcctcatat tccctctgaa agaaaataaa aggtcaatat agcatacact   13620
aaaatcaaag tgagggtgac tagatgacta aaactacaaa cttaccttca tagctctacg   13680
atctttgaca aatgatgtct gaactttatc cttcaagtaa tctattttcg cagcaaagta   13740
ccattctggt gcacgaggct ctatgctata tttcttgcaa aatggtaccc atttacgagc   13800
aaactctgat gtttctgcaa gtgattcaaa tgataacata gcagcaccat catcagaaac   13860
ataacaggac accttgtcaa ctgggtagtc aacagccaga atagagagca ctgtgttggc   13920
tgtcacaagg ggtggctcct tcaaggggtc aacagtactc acgaaaatgt caacagcagc   13980
```

-continued

```
taactgtgat ggctcacctt cacgatcata tctgtcccaa aaattgacca tgatcaaatt      14040
aaaatgggaa acagtatagg caaacaatcc tttgagtaat tgcttcagaa gaatggggaa      14100
atagaactta ccttaaagca agcctgtcga ggtaggtttc acggttcaca ggaaaccact      14160
tgggaaactg atccaaaatc caggataagg caaaccagat ctcacatatc acagagacca      14220
gccatagagc aaaggcattt ggcactgggt ttgttatacg gtaatgcaag aagagacaaa      14280
ggataacaag ccgcagcata ataaccattc tgtaaggatt gatccgtgat gaaggaattg      14340
aaactttcct tgacagaggc tgcctcgctt cgtcattcct gtacaataaa taaagaattg      14400
gaaaatgagt atcaggacat tgcttaatag gaaaaacgct cggtacacca cgacagaaca      14460
aacaagatta caaaacaaga actcacagca gagcctcatc tgctaggata tctgtgctgg      14520
catcaatatc tactccacct ctttcagaag cagcctgcgt gctgacagga ccagtattct      14580
tctcttgctt cattttccag ccatcaactc tctccttcca agctacattc ccgagtccaa      14640
caggatccac aatccttcta tttgctgcag cgtgaatgac aacaacagat tttattgttt      14700
agagttttga cataaaagag aagcctaggt acaaatatat gtgttggcga gagagttaga      14760
aataaaggat atttacgtga ttgattgaca tctgatgaat agggaaggcg ctttccccca      14820
gcgatagtag aagatacaga gaggcgttca ggtgaggcag cagaaaactc tcctgaagtc      14880
tgtaaataag caaatgacaa aatcagattc caaaactaaa ttgcgtgagg atgcgaatgc      14940
ttaagaggga agaatgaaca gcaatgcctt acatcttgtc tgctcgtgag acgaggaaga      15000
tgattgtgag agacctcttt atcatactgg ggttcccccca tttcctctcc cttcccacga      15060
gtaagatgcc aaccaagcat ccgctctgaa attttctcct tctgagggta gttgaactca      15120
acagtacctt catcagctaa gccatcctcg tctttatcac caggaatagc aggactacct      15180
agaatcagaa attagcaaat tgctataaat accaatctga tccaaaattc aaaacatact      15240
gataaactat cgatgaacaa tgaagacagt atacttcaga aggatcaaaa gagaaccttt      15300
gagcctcttg tatctggttt tgcactgagg acaagattga ttcccatctt tcctctcata      15360
ctcgtagcaa ggccgacaaa ctgggaatga acaaatatca caagccacaa aacgatctcc      15420
atcaacagtc ttgccaacat tgtcactaca gatctggcaa gtctgcggaa caatgttctt      15480
catcggcttt ccctacaaat caagtcgaat caatgaagcc aaaattagaa acctcaacag      15540
aaaatttgaa atcagatctc tccaatacac aattcaacac ccaaatcaat caatttcagt      15600
acatataatt cctgatttcg ataaaggtaa gtataatgat gaagcaagag tcaaaaaagc      15660
ataccgcggt ttctccttcg gattccattt gtcacttagt tgcttccaac accgaaacgt      15720
cggaatagtt caaatctgat cggaattatc aaaaacagaa actacgatta gatctgagga      15780
gatccgagta aaggaagtca aatctgagaa tggatcatga gtgtaagaag agttaaaagc      15840
tttaccatga gatctgaaga tggagtgtgg tgatgtgact ctctgaatct ctctcaatct      15900
ggatccaagc tttcttctct acagagagat agtttataag gaagacgaag aggagaatct      15960
tgggatggct aagaagatgc aaagagcaag ctatttgtct cctctactcg tcactcttcc      16020 agattttaa aatattaata tatttgtcac aaatcataat ccaaccaagc aacaaccacc      16080
accaccaccg acaacttcca cagtcgattt ttttctagtt acagttttac agtggctgta      16140 aaaaagtga aaaacggcc gataaacctt taaaatatcc ttagaaatat attatcatcg      16200
aattagtgac taaatcaaaa tagtaattga tatttgatag tgatataact aaaatagaag      16260
tgtgaagaac acaacaaatc acaagtagtg gggtaaagga tattcatcgt cactaacttt      16320
cttacagata aaacttaaaa agtatttgcc gacaaaaata aaacttcaaa atattaatta      16380
```

```
atcaacggat tagtccaatg aataaatcaa aatatattga tagtgatgct ttacttacta    16440
gtatatcaaa ataggctaaa accagcgggc tgaaaaaata aaggtccaac tctagtatca    16500
tcaagcccaa cagaatcgag aaaatgggtt tgttggactt tgcagacaaa attggtatat    16560
gttcggttta cgttatttac gagagaaaat tgaatcgaac cgaacccaat aattaatagg    16620
tcaaactttg ataactggtg gtgcatgtgg agatgtgtgg ccactagtgc agcaaagaac    16680
agactgtcag atagacaaaa gaagaaaatg gcaaacattt gaatcccaaa gagcgccact    16740
ttctcttcgc tatccgacaa atcttccctc ctctttgtcg tccctttaaa cctttccacc    16800
ttctgcttcg taactctcgt accctagcaa tcctctactt aaaccttcct ttgtttctcc    16860
ttcacttttc ctgtaaatct gctcttttgt tccctcgatc atatcaattt tcaaggtcag    16920
tgaaatctca tgtttatttg gtcctatgtg aatcagattt cagggtttga tatttgtttg    16980
ttccgttgat gtgttttgta gatcttatga tctgagttac ttgctctgtt tttctgagat    17040
ttatggaggg tctttgtcta tgtttcttca ccgttgcaaa tgagttataa tttctgttta    17100
catgtagtga aaaagttcca gttctgtgac ataagaaagt cttaaaattt acgcaaccct    17160
agttttttta ttttctaaga tttcaattaa agaacattag cttgtctctt catgatagtt    17220
ttccactgat tattatcaca acttttttttt tgttagata tttttaatcg aaattattgt    17280
agagataaat ataaatacgt tttttttttt tttggtcaaa aaatataaat acgtttagtt    17340
atagctaaat cttaggagta taaaaaaaaa aaaagtaaat aaaaatctta ccagttttta    17400
tatctcgtat atcttctgta ttttttagggt ttttctgtta catcattcta tgtttacgtt    17460 tctttgatttt ttttttgctt gatcattttt aagttgattc gcttttttgtt gtttaagtgt    17520 aatggatttt acaacagttg aggtcccaga tgagtggcca cataattcga attcctttgt    17580
ggacatctca acaggtataa ccgtataatt cattcatgtc ttattttggt tgtgtgcgtt    17640
tccgttcaaa cgtagaaatc ttattagaca tatcaattgt caagtttcag atcacaatgg    17700
atcttcacct cctgtaactc caaagtctga tacagtagct tccaactttg accaaggaag    17760
ttctgatgtt tctggcaatc atgattctaa ctcttcttat tccgatttag attcggacac    17820
ggaggccttt tactcatctt ttaaccatca cctcgtatca ccagggtcaa tggatagcca    17880
tgacttatcc ccggagaaac aaatgagtta tgaagaattg atgaagaaat atgtccagtg    17940
tgaagaagag cttaggacta cgagtttgaa acttcaagaa tttgagcaag agattgagaa    18000
actaaaggag accgagaaaa aagaatcggt tgttctgttt ggcgagtatc tacgtggtga    18060
gcgagaaatc gcacaaggag aaattgcgat tagggacata gctattgaga ctgagagaaa    18120
gcgagttctc gaggtgcaaa gacaggtggt tgatttggaa actgagcttt cagacttaag    18180
tttcaaattt gagcatctag tgaatgagca tgaggtgagt agggactgtt tagatgtgtc    18240
attttctgaa atctctaagc taagggaaat gttgtgtgat tgtcagcaaa atttctctat    18300
tgagaaaaca aaactggtag atcagataaa gcattctgag gcagagaaaa tggagatgca    18360
gaggaaagag gttgagttgc aagctgaaat cagtgcattg aagacagact ggccacacg    18420 tggtgagcat attgaagcat taaacaaaga tttcgacaag cacaagctga ggtacgacat    18480
gttaatggca gagaaagacg gagtatgtgc tgaagtagac aatctaaaag cagagatgag    18540
atcaagagac atccaaattc agcaaatgga ggagcaactt aaccagctgg tctataagca    18600
gacagagctt gtgtctgaat caggaaatgc caagaacact gttgaggaac tgaaagctgt    18660
ggttaaagaa ctggagattg aagtagagct gcagagtaag gccaagaaaa ctgtggagga    18720
```

-continued

```
actgagagct acggtctggg aaatggagaa gcatgcagag ttgcagagga atgcgatatc    18780
acaaggagag gaagagaaac gagaggcgat tagacagctt tgtttctctc tggatcatta    18840
caaaagcgga tataaacagc ttttgtggta tctttcgggc aataaccagc aacatcaaac    18900
aaccatggtc gtgtgagttt cgattgaata ctcttatcat ttctttagtc gttacagtct    18960
tatgtctttc tttgtctcgt catgttttt tatgttattc tgagttatgt tctctctcaa     19020
actcttggac attaatctta agatttcttt agtaagaagc gcaatttata tgaaattcta    19080
gcttcttttt tttttgtgc acctatatga aattctagct tggaaatgct tttatatatg     19140
tggctttaat tttgtgtgat tttataaaag tattttgaa cttagggtat ctacaggtgt     19200
ttctgtctgg agtttttatt tgtgcttatg taatagtgac gtaaagccta agtaattaaa    19260
agtgagagag aaaaagtcaa aagccaaaca caaacctaat cctccaatat ctcaacttgg    19320
ttgactctct caatacaagg attggagtta atgtgaaata ctaaggactc aattattatg    19380
gtccttgatt tatgattttt gttcagaaaa atttagtgaa cacaaaaaca aattcttctc    19440
gcccaaacca gtgaagaaat atgaaatcta aaatttaaaa ctaaatctga accagagaag    19500
taatattccc aaaatcaaag ttgaacgagt ctgatttcta tactgcgtct atgtatatgc    19560
tcccagttcc atttctattt gtgttgaaac ttttaagtat tggtcaaaca atttttgttt    19620 tttttttgggt tttaacaatt tataataaga tctgactatc tcaggattgg tcatgttcaa    19680
caagacttag tttcatctaa tccacataaa gtaaataaaa aaaatctca agttatagtt     19740 tgatattata ggtctattac gtaaactttc ctccatatgt aacgatatat gatcgaccgc    19800
gtaaagatgc acgcgcatgc aaatatttta atttgattgt tttagtttat gctttcatgg    19860
tagtattaaa gttgtaaatg tgattgcatg tgtgagtgtg tgaaaggact ttgcaagacc    19920
gctggctacg aactttatta gttagataca acaaatttat caattatcaa tcttaaaaga    19980
tagctaaaga aaacgttact atgggcccctt tttctttctt taattctttc atatggaatc   20040
tattattaat taaagacatg tattaaagaa tttcaggtgt aaaagaatag ttttttgctt    20100
tgaggtgtct atctttattt ataatcggaa attttcaagt aaaaagaaat agactctcca    20160
aagcataggt agaataattg aatattctta tcaattaaat cgtctatagt agccaattat    20220
gattgcaatc gttgtgcgaa tataaccagc atggtatata tcacaagttt ttagttagtg    20280 aatttttttag ttatttcaag agcttgttct gtagaataaa ccaaaaacta aagaaaatc    20340 cattctattc aataccataa cttcatgtgt tcacgaaaca tcatgggaac acagtaaata    20400
gaaaaacaaa atcaatttat aactatatat gaatgttgtc aaatgggagt tgacctccaa    20460
tattatcttt tatacatttg aaactttaat tttgactttt ttttagtaag atagttttg     20520 ttcatgtcct gaatgttagg taacagctag cgatttgaaa tagaaataaa catttacaaa    20580
ccatgtagtg gtccaaacca ttgactcaat taaagagtca acgcataatc gaatttgtaa    20640
tctgtgaaga agaagactcg aatggtattg aacttgattt gatttgattc gttttgtgaa    20700
tcgtatcccg ttagtcattg gattgtgcag agaaaacaaa tattgaagca acctctaatt    20760
aagtctacaa agaaatagga caccacaaca aaggttgact tttacagaat cacaaagcca    20820
aaacgataat ctagaaagta gagaaactag acagcacaaa acgataaaag accgagtctg    20880
tcgaccatta ccttagtttt ttttcatatc gttaaaaaat aatgtgatat acatgtacgt    20940
taatacttaa tatatactat ttgacttgag atagccctac aaaacttttta ttcatttatt    21000 tctcacaagt tccctaaaac tttatgaacc aattttgaaga ttaatatttt gttacgttgc   21060
tatcaatttc aaattctttg taggtgctat atttgaaaac tggtttcata cctaaaaagg    21120
```

```
ttatgaacca aagactcaac ttgtctggtt ataaataaaa gtgattgaaa acactcacac    21180
ggctagtgaa ttctcattag aaaaatgaaa agttcgttaa attcgaccag tgatataaat    21240
atatatacga aaaacatatg atcattatgc tttttgtcag gtcctagaaa taaatatgtg    21300
gaacccaatt catttcaaca ttcacggtaa tttaatttcc cttggcaaca tttagtcatt    21360
taccggaata ttcaaacttc gaatgttagg aaatatttaa gaaggtaatg gtaaaaagta    21420
agaaaaaaag gactgggatc aataaatgag aaaaatggaa gtagtagtgg ggctaaaatt    21480
tctctatcca aaataaatga aacaggcgcc gacattaaca acaccattcc atttataact    21540
ctttatccaa attttttattt agctgaaccc aatttactct ttctcttatc ttcctctact    21600
taattcttct aacaaagctc tgttgcagat gctttcttta gaaaaaaatt gggccaatat    21660
tgtttattga aaagatcaac aacagactgg gttttgttta agaaagaata gtgattagag    21720
aacgagtcgt tgatgttcta attgacttgc aagaatgaaa aaagatacca aaaaattcct    21780
caaagagata ttaaaagaa aaaactttt agacacggaa aaagagagac ttttctcaga    21840
ggaaaaaaac aagaaaagag agaaaccata gtaaaaaaaa aaaaaaaact gtctgtccaa    21900
cgatttgttt ttgtttttttt gtctctgttc tctcaattct tcttcttctt cttctacttc    21960
gcccccacga caagaaattc tcctctctat ttctatctca ttctttctct ctctctctat    22020
aaaatcttca acttctgggt ttattcttcc acaatccctc gagttataat aactctctgc    22080
aaagagtttt actttgattc ttctgtggag gatcttacac aatttttcatg gcttcttgaa    22140 tcatgtaatc ttttccttct cgccattttt catctctacc cggatccgta accagctctc    22200
agaccagacc cggttatac catttctcct ccttaaaagt cacaccgcgt tgaccttctt    22260
cctctggtct cctctcccat tttctttttaa agaacttcac aaagtttcaa tcttttactt    22320
tggttcctct ctctctctct gtttattagg gttctgggtt ctgttgatga tgattctcta    22380
actaatgagg tagagttata acccaaaaat aacaaaagta gagttaagtc tttgaaatttt    22440 ggtaccaaca atggcgagcc agacgggtca gaaaattcgg ttggtgaggt gtcccaagtg    22500
cttgaagatt ctacaggaag acgaagatgt tcctgtttat cagtgcggtg gttgttccgc    22560
cattcttcaa ggtaactttc tttccatttc gattttgcct ctgattataa tgtgaactct    22620
gtccctgaat ctggctttgt tctactcctg gttgtccatc tgtttggatg tctgagctca    22680
aaccagttgt gttttgtggc atgatctctt tcattattaa atttggttgt tgcttctttg    22740
attcagcgaa aaggcggaac attgctccaa gcagtacacc aagtgcagga gagacagaga    22800
gggctcaagc caatgagccg caaagcgtac ctgaaaccaa caatgtgtcc agcagctcgg    22860
ggcaggacac ggttctgccg tcatctccag gtcgttccgt ggaccaagag tatgagaaag    22920
gtaggaatgc atccatggag tctacggaga aggagcttga tgacttagag ttatctaatg    22980
gagatgggac aaatgaaatt caagagcagg aatgttcact tggtgattct gagaagaatg    23040
aaagagaaga caactccaga ttggagtctc atatgatgaa caccgtagca gaagctgcag    23100
gatctggatc tagctctgga agcttgagcg ttgatcatgt ggtggctgca agagcgagta    23160
atccatccgg taactctgag atttcaccgg atgcttcccc cgtagaagag aagcaaagcc    23220
aacttgacat tcttgcaaac aagactcctt ctgcttatga tgtggtggct gcaagagcga    23280
gtaattcatc tggcaatgct gagatctcac ctgatgcttc ccctgttgaa gagaagcaaa    23340
gccaacttga ttatcctgca aacaagactt cttctgctta tgatgggagt gagtcttcct    23400
ctgacgaaag ggaaggccaa cttctcgatg atgacgaaca atggaatgct cttcagaaaa    23460
```

```
taagatcagg caaatttgag atgcatagat accctgggta taaggagcaa ggcgctagtt    23520
cctcctcccc tttctctgag aataggcgca atgggattac cacatacaac gagcggcatc    23580
agaacaggtc tctacagcta gagggaccag gagggcgcct tggcagacaa gggaggagac    23640
atgtgacaga acaacttcgg cctgacatgc ctttctatcc gagagaatca tacacacgtg    23700
gaagcccttc ccatccgtca catgatgagt ttgatcgcta tccccgtgca cactcacttc    23760
aaatgccttc atacgctgga ggcatgaacc acgattttgt tgactatatg tatcacaaca    23820
acccaagggc aagaggtcag ggccaaggaa gtaggatctc aggtgaaatg ggaagaaacc    23880
atggcggttg gtattcaggt cagcttcata attcttacag ttcatattct gcaagtccac    23940
agagaccaat ggaacaacct gagtatcatc cgagatggag cgtgagata gtctcagacg     24000 tggaggatca tcagcgtaat agacatgctg gccaccacca tgagttacag acccgtcgtc    24060
taagagagag acaacgtgtg gccaagcgtc atgtccgtcc aacagctggt ggggcacctt    24120
ttgttagctg ttacagttgc tcagaaaacc tgcagcttcc tgtagacttt ctcattttca    24180
agaggaaaca tcatcttctc agatgcggca cttgcaccac tgttctcaga ttctcacttc    24240
agtccagaaa tcatttagtt cctgcagtaa cacatgacat aaatgctaat aggaatagca    24300
attcaacatc agagtctccc atagacaaag ctccctccaa acctgaaaag ctgagatcct    24360
ctgttcagga tgaggagcta cctgtggcta gaggctctcc gcttcaccga ctaatgggat    24420
attctactgt aagccaagtc tttaaagttt cacagcgtcc tccttctata tagatctctg    24480
cttcagatga agcaacgaga actatgaact tctgagaatc tgagatgaa agttttgcca    24540 ttgtttgcca ttctttattt cacttctgtg tataggtaaa agatttgtct ctgcactttt    24600
gtttaaagta gaaaccatga cacttgtgaa aaattataca aaaaaataga agaagatata    24660
gttcatctgt tgtatatagt catgatatgt ttgtaacaag attgaattca tcatcgttct    24720
tggcttgata atctactata acattaccac ttgtaaataa ataaaaagtt tgaataggtt    24780
tagtgaagta tatttgcata aacttagttg aagctgtcct tgtatccatt cgtcctcttg    24840
ttggacgcga tagagatccg ctgatcctgc agcatgttca ggtttggggc taatagtctt    24900
gtgtatcgat cgaagtacag aagttgcttc aacagaagtg caaactctct cgggaactta    24960
agaccatatg attcgctaac acgcacctat aagaaagtga acttattttc aactgctgaa    25020
agctcaaatc ctggggttta tcttaactca atgcaacttc tatatcctct taacaacttt    25080
caaaccaaaa aaaatccttt aagaaattac gtctaactgc ttaccaggtc gaggaaaaga    25140
gcattcatct gtctctcatc cataactacg ttagcagcaa cagcagtagt gtctgaattt    25200
gttccacgag ctgtagccac tactatctct gtatctagtt cctgcaagaa gagattcact    25260
tttctctata agattagcca aagttgttgt agttgttttg cactacagtt cggaaagcaa    25320
atcaagctgg ttcctctgaa cagatgtagc tggttacaga gagccatcat agtcagtaaa    25380
gagtaaaatt tcttgcctgg atagatgaga acatcttttc caagtctttt gcaaaagctt    25440
tgccatcaac atctctgttt gtggcgccca tttgaatcaa agctgaggcc atggattcat    25500
attcttcagt tgcaatagac gctaaaaata cttccatagc agcccatgtt ttgggggata    25560
tccgaccaac aatgcctgaa aaaatgtgg atacttactt gaatacacaa aaaattacca     25620
ataaaaagga agagtattta tggaaaaaga ctgcattttt ctgtattaat agatgagtca    25680
gaggtaagta ggcaagaaat gttgcactaa ttaggcttga gagagtatga tttaccaaaa    25740
tcaagaaacc caatccggcc atcacgcaac agccataagt ttcctgcatg tacatcagca    25800
tggaagcttt cacaagcaag taagcttcca aacctgcaag ttacatcaca tgaagattca    25860
```

```
ttttactaac agctacattt aggagggaga acaatcttaa tcataatatt gaatttcaaa   25920
gatcttacca cacattaagc gcggtaataa ggctgttttc gggactggaa acaagtgatc   25980
ttatagagtc cagatcagtc agaggaactc catatagcct ctccattgta agtacccgcc   26040
ggctgctgca gtacttatat actcttggag cagtagcttg ccctgtcaac cccatggttt   26100
caagatatct cttaaatgac tcaatgtttt gagcctcctt attgaaatct acttcttcaa   26160
gcattgactc acgaatatct ttgacaattc caacctatcc ataggataat attgtttaga   26220
gagtatctta agagcgactg caaatcaaat acagaggaga ttaccagtga agtacggcta   26280
aactcaggac taaggaactc aaatatacgg gaaacaacgt agataaagtt caaatctgcc   26340
actaagaaat cttctatccc aggcttcaag actttaatca caacatcctc ttgggagcct   26400
cgaagccttg caccatggac ctggtcatga tgattcccctt aagcagaaga agagtacatg   26460
aacaaaatga attttgatca ttgaagtaca agtagaagaa cacacttgtg ctattgaggc   26520
tgatgcaatt ggcgtagggt caacatattc gtatacactt tcaatgggtc tcccaagctc   26580
ctcttgcaag attttacgaa tttcttcaaa tggcacagga ggagctttgt caaagcagtt   26640
ctgaaattct ttgacatatt ctggtgggaa caaagttggc gcagatgcta taaactacaa   26700
attcaaagat acattacaag tattgttaaa tggatagaat aggaaatata tagaagcca   26760
acaaaatatg ataactaagc ttactttaga catacacagt tcacatggtt ctagatattt   26820
acatgatatc atcagaggat acaatatgct ctacatttag caacatgatt tacctggccc   26880
agcttaatgt aagtagctcc catgcgttca aagagtttcc tcaaatatag aggagacagt   26940
agaccaagct gcaattcact tggtaatcca ccagacgcgc ttgtagactg cagcgagtga   27000
gagagtagtt agcaatcaaa gatagtttga catcataagc aaaaagataa tttcagccac   27060
cttagataaa tcatttagcc actctcctcc aaccccctaca aaggcttgaa caccttggac   27120
aaggcgtgtc acacctcgtg gacctgtgtt tatcgatgtc tgaactatat cctcaaccaa   27180
tttgggcaat ttctctatct ggcctgcatc aaaagccatg taaacaagta aatggatcaa   27240
taaactgtca tccaatatgt agattttac aaaataaatc caataagcaa caaagaatac   27300
cctaacgaga tacaattcag aatcatagat gtatacaatg agattgagtt tacaagaaga   27360
aggaaatttc tgtactttga agacgagaag tgaaaggtc ctgagtttgc gaatactggg   27420
ctgtaagaac aaaacccttg aaattcctgg ctccgatcat cttcttagac gttcctgaca   27480
cagttctcgc gacgggaaac tgaaaaatga agctatcgag attgagcagc gagtaaagga   27540
cctttgcaaa ttttggtagc taagccataa agagcagatc aaggaaacga ctttactgaa   27600
ggaaagagaa gagaaaacaa gtaaacctga gaatggtgaa ataacggtaa ccgcgtgcca   27660
cggaaagctg agaccgccat cgttcgccgg cgattgaagc agcagagaca agacactccg   27720
gtcaagcttt attactcaca aaacgcacag aaaagcgaca ccgttttgta tattttgaaa   27780
attgaaaata tcctgaggcg gagtgaaggg gaatatgcca cgtggaaacg tgtaagtggt   27840
tgttttcctc ctcacaagtc acaacatatt cgtgaaaaac tctcggtacg attcgatttc   27900
cggttaacct cttttaaatc ccattaaacc gaaccgtttt tgcgacgctg gaggagaagt   27960
tgagataacg cggttttaca taaatacct tataaaaatt gagaaataac aaaaccattc   28020
aaaccctaac cactttcacg gaacctcttc atcttcgtct ctctgtcttt tttcttctct   28080
caacgccgtt gattcgccat cgtcgctacc ggtgagattt tccttcgatt gtctttcttt   28140
tattccatca attcgctctc tttccatctg ggtttgtgct tgtagcttaa aaaaattgat   28200
```

```
tatagagtca gaattgttta tcacttaaga taatgagttc tgagttataa tgattcctga   28260
actgatatgt agaaacttca acttttattt gtttctacga ttcatccttg tttgctttag   28320
ggttcttcta ttctttgtag gataagattt gtttctttgg cttgtttatg tttgcttctt   28380 atcctctttta ttcatcctga gcttgttata ctggggaaac ttgttgtatt atactaaggt   28440
ttctgtttct cttctggata atgaataagg atatttgctc aattacacaa cttggaattt   28500 tgttttatg gattaatggt gtctacaaag tcatcttctt tagttctgta tctatctagc    28560
aaacgagtaa acttggtgtc acttgatgtg attcagtgac ttgctcgatt ctgacaagat   28620
gcaggaaatt ctgaatgtat ttgtaccagc ttagttatag ctatgtataa tgtatatcga   28680
aatacatgtc ttatgatatc tgtagtcttt cacagttact aatatatcct tgttttattg   28740
ctgcagattc tcttgaggtt tacgactttt ggactaatct cctctgtgga gagcaatgac   28800
taaaactcgt gggactgatg taagttttga tttccactgt taacttttta tcatctaata   28860
ttttgttaat ctgccattgt aagtcttgat tctatagttt ttatgaaact tggactatga   28920
gtccttagtt tattatttgt catttctcca aaagggcttt tttctgattg tgattggttt   28980
tggttattgt tgtagatgac aaagaaaaag ggtaaacatg tttctgaaat ggatttcaag   29040
actcatcagc atactgaatt tttcgataag ttgatagagc tcacgcctgc tagattctac   29100
ttacctgatg agacagaaag gaaatggtat ccaggtctta gcaaggctca aaaagctaga   29160
gccaagaaaa aaacaaatga caacctaaag aaggcgaaga gagataagtt ggacccagag   29220
aagtctgctt tgacgactct cgatttactg aaggagaaga tagagaagga aagattggct   29280
tcacagaagc ag                                                      29292
```

<210> SEQ ID NO 24
<211> LENGTH: 3682
<212> TYPE: DNA
<213> ORGANISM: Arabidopsis thaliana

<400> SEQUENCE: 24

```
ggactcgcgc gcctgcaggt cgacactagt ggatccaaag aattcgcggc cgcgtcgact     60
acggctgcga gaagacgaca gaagggggatc ccaagattct cctcttcgtc ttccttataa   120
actatctctc tgtagagaag aaagcttgga tccagattga gagagattca gagagccaca    180
tcaccacact ccatcttcag atctcatgat ttgaactatt ccgacgtttc ggtgttggaa    240
gcaactaagt gacaaatgga atccgaaggg gaaaccgcgg gaaagccgat gaagaacatt    300
gttccgcaga cttgccagat ctgtagtgac aatgttggca agactgttga tggagatcgt    360
tttgtggctt gtgatatttg ttcattccca gtttgtcggc cttgctacga gtatgagagg    420
aaagatggga atcaatcttg tcctcagtgc aaaaccagat acaagaggct caaaggtagt    480
cctgctattc ctggtgataa agacgaggat ggcttagctg atgaaggtac tgttgagttc    540 aactacccctc agaaggagaa aatttcagag cggatgcttg gttggcatct tactcgtggg   600
aagggagagg aaatggggga accccagtat gataaagagg tctctcacaa tcatcttcct    660
cgtctcacga gcagacaaga tacttcagga gagttttctg ctgcctcacc tgaacgcctc    720
tctgtatctt ctactatcgc tgggggaaag cgccttccct attcatcaga tgtcaatcaa    780
tcaccaaata gaaggattgt ggatcctgtt ggactcggga atgtagcttg aaggagaga    840 gttgatggct ggaaaatgaa gcaagagaag aatactggtc ctgtcagcac gcaggctgct    900
tctgaaagag gtggagtaga tattgatgcc agcacagata tcctagcaga tgaggctctg    960
ctgaatgacg aagcgaggca gcctctgtca aggaaagttt caattccttc atcacggatc   1020
```

-continued

```
aatccttaca gaatggttat tatgctgcgg cttgttatcc tttgtctctt cttgcattac    1080
cgtataacaa acccagtgcc aaatgccttt gctctatggc tggtctctgt gatatgtgag    1140
atctggtttg ccttatcctg gattttggat cagtttccca agtggtttcc tgtgaaccgt    1200
gaaacctacc tcgacaggct tgctttaaga tatgatcgtg aaggtgagcc atcacagtta    1260
gctgctgttg acattttcgt gagtactgtt gaccccttga aggagccacc ccttgtgaca    1320
gccaacacag tgctctctat tctggctgtt gactacccag ttgacaaggt gtcctgttat    1380 gttttttgatg atggtgctgc tatgttatca tttgaatcac ttgcagaaac atcagagttt    1440
gctcgtaaat gggtaccatt ttgcaagaaa tatagcatag agcctcgtgc accagaatgg    1500
tactttgctg cgaaaataga ttacttgaag gataaagttc agacatcatt tgtcaaagat    1560
cgtagagcta tgaagaggga atatgaggaa tttaaaatcc gaatcaatgc acttgtttcc    1620
aaagccctaa aatgtcctga agaagggtgg gttatgcaag atggcacacc gtggcctgga    1680
aataatacag gggaccatcc aggaatgatc caggtcttct tagggcaaaa tggtggactt    1740
gatgcagagg gcaatgagct cccgcgtttg gtatatgttt ctcgagaaaa gcgaccagga    1800
ttccagcacc acaaaaaggc tggtgctatg aatgcactgg tgagagtttc agcagttctt    1860
accaatggac ctttcatctt gaatcttgat tgtgatcatt acataaataa cagcaaagcc    1920
ttaagagaag caatgtgctt cctgatggac ccaaacctcg ggaagcaagt ttgttatgtt    1980
cagttcccac aaagatttga tggtatcgat aagaacgata gatatgctaa tcgtaatacc    2040
gtgttctttg atattaactt gagaggttta gatgggattc aaggacctgt atatgtcgga    2100
actggatgtg ttttcaacag aacagcatta tacggttatg aacctccaat aaaagtaaaa    2160
cacaagaagc caagtctttt atctaagctc tgtggtggat caagaaagaa gaattccaaa    2220
gctaagaaag agtcggacaa aaagaaatca ggcaggcata ctgactcaac tgttcctgta    2280
ttcaacctcg atgacataga agagggagtt gaaggtgctg gttttgatga tgaaaaggcg    2340
ctcttaatgt cgcaaatgag cctggagaag cgatttggac agtctgctgt ttttgttgct    2400
tctaccctaa tggaaaatgg tggtgttcct ccttcagcaa ctccagaaaa ccttctcaaa    2460
gaggctatcc atgtcattag ttgtggttat gaggataagt cagattgggg aatggagatt    2520
ggatggatct atggttctgt gacagaagat attctgactg ggttcaaaat gcatgcccgt    2580
ggatggcgat ccatttactg catgcctaag cttccagctt tcaagggttc tgctcctatc    2640
aatctttcag atcgtctgaa ccaagtgctg aggtgggctt taggttcagt tgagattctc    2700
ttcagtcggc attgtcctat atggtatggt tacaatggga ggctaaaatt tcttgagagg    2760
tttgcgtatg tgaacaccac catctaccct atcacctcca ttcctcttct catgtattgt    2820
acattgctag ccgtttgtct cttcaccaac cagtttatta ttcctcagat tagtaacatt    2880
gcaagtatat ggtttctgtc tctctttctc tccattttcg ccacgggtat actagaaatg    2940
aggtggagtg gcgtaggcat agacgaatgg tggagaaacg agcagttttg ggtcattggt    3000
ggagtatccg ctcatttatt cgctgtgttt caaggtatcc tcaaagtcct tgccggtatt    3060
gacacaaact tcacagttac ctcaaaagct tcagatgaag acggagactt tgctgagctc    3120
tacttgttca atggacaac acttctgatt ccgccaacga cgctgctcat tgtaaactta    3180
gtgggagttg ttgcaggagt ctcttatgct atcaacagtg gataccaatc atggggacca    3240
ctctttggta agttgttctt tgccttctgg gtgattgttc acttgtaccc tttcctcaag    3300
ggtttgatgg gtcgacagaa ccggactcct accattgttg tggtctggtc tgttctcttg    3360
```

-continued

```
gcttctatct tctcgttgtt gtgggttagg attgatccct tcactagccg agtcactggc    3420
ccggacattc tggaatgtgg aatcaactgt tgagaagcga gcaaatattt acctgttttg    3480
agggttaaaa aaaacacaga atttaaatta tttttcattg ttttatttgt tcactttttt    3540
acttttgttg tgtgtatctg tctgttcgtt cttctgtctt ggtgtcataa atttatgtgt    3600
agaatatatc ttactctagt tactttggaa agttataatt aaagtgaaag ccaaaaaaaa    3660
aaaaaaaaaa aaaaaaaaa aa                                              3682
```

<210> SEQ ID NO 25
<211> LENGTH: 19
<212> TYPE: DNA
<213> ORGANISM: Artificial
<220> FEATURE:
<223> OTHER INFORMATION: Primer Sequence

<400> SEQUENCE: 25
ttagccatcc caagattct                                                  19

<210> SEQ ID NO 26
<211> LENGTH: 19
<212> TYPE: DNA
<213> ORGANISM: Artificial
<220> FEATURE:
<223> OTHER INFORMATION: Primer Sequence

<400> SEQUENCE: 26
cttcaagggg tcaacagta                                                  19

<210> SEQ ID NO 27
<211> LENGTH: 19
<212> TYPE: DNA
<213> ORGANISM: Artificial
<220> FEATURE:
<223> OTHER INFORMATION: Primer Sequence

<400> SEQUENCE: 27
taccgagcgt ttttcctat                                                  19

<210> SEQ ID NO 28
<211> LENGTH: 19
<212> TYPE: DNA
<213> ORGANISM: Artificial
<220> FEATURE:
<223> OTHER INFORMATION: Primer Sequence

<400> SEQUENCE: 28
ccagcaccta agtttcaca                                                  19

<210> SEQ ID NO 29
<211> LENGTH: 20
<212> TYPE: DNA
<213> ORGANISM: Artificial
<220> FEATURE:
<223> OTHER INFORMATION: Primer Sequence

<400> SEQUENCE: 29
gttcagttcc cacaaagatt                                                 20

<210> SEQ ID NO 30
<211> LENGTH: 18
<212> TYPE: DNA
<213> ORGANISM: Artificial
<220> FEATURE:
<223> OTHER INFORMATION: Primer Sequence

```
<400> SEQUENCE: 30
tcattccgac caaaagtt                                                    18

<210> SEQ ID NO 31
<211> LENGTH: 59
<212> TYPE: DNA
<213> ORGANISM: Artificial
<220> FEATURE:
<223> OTHER INFORMATION: Multiple Cloning Site

<400> SEQUENCE: 31
ggactcgcgc gcctgcaggt cgacactagt ggatccaaag aattcgcggc cgcgtcgac       59

<210> SEQ ID NO 32
<211> LENGTH: 28
<212> TYPE: DNA
<213> ORGANISM: Artificial
<220> FEATURE:
<223> OTHER INFORMATION: Cloning Fragment

<400> SEQUENCE: 32
tacggctgcg agaagacgac agaagggg                                         28
```

MODIFIED CELLULOSE SYNTHASE GENE FROM *ARABIDOPSIS THALIANA* CONFERS HERBICIDE RESISTANCE TO PLANTS

PROVISIONAL PRIORITY

This application is a continuation-in-part of, and seeks priority to, application Ser. No. 09/686,234 filed on Oct. 11, 2000, now abandoned, which in turn was submitted in reference to, and sought priority of, Provisional Application No. 60/159,369 filed on Oct. 14, 1999 that bears an identical title.

U.S. GOVERNMENT RIGHTS

The United States Government has rights in this invention pursuant to Contract No. DE-FG02-94ER20133 between the U.S. Department of Energy and the Carnegie Institute of Washington.

SEQUENCE LISTING

The contents of the paper and computer readable copies of the sequence listing submitted herewith are the same.

FIELD OF THE INVENTION

This invention relates to a mutant gene coding for isoxaben and thiazolidinone-resistant cellulose synthase ("CS"), and the process of imparting such resistance to a plant crop.

BACKGROUND OF INVENTION

The ability to modify microorganisms and cells of higher organisms by genetic engineering has made it possible to change certain of their specific characteristics and thereby alter the response of those organisms to various agents. Of particular interest are the responses of organisms to agents used because of their cytotoxic effect. For example, many compounds used in agriculture are directed to the killing of pests, weeds, or the like. Often these compounds can have a relatively long residence time or extended residue in the plants subjected to treatment by the compound.

In many situations it is desirable to differentiate the species to be retained from the species to be killed. For example, it is often necessary to selectively destroy weeds, yet have minimal impact on the economically valuable crop plants. For the most part, broad-spectrum herbicides have a sufficiently adverse effect on crops that their use must be limited to emergent use or careful postemergent application.

Some weed species are simply resistant to today's herbicides, increasing the importance of developing the production of effective herbicides. Moreover, as some weed species are controlled, competition is reduced for the remaining tenacious weed species. The development of genetically engineered herbicide-resistant crop plants could significantly improve weed-control by allowing fields to be treated with a single, concentrated application of the herbicide. Therefore, a one-step procedure could eliminate costly and perhaps ineffective repeated low-dosage herbicidal treatments, such as have been required in the past to avoid damaging conventional crops, but which may have also induced the emergence of spontaneous herbicide-resistant weeds. Herbicides with greater potency, broader weed spectrum and more rapid degradation after application would avoid the problematic persistence of the chemical herbicide in the soil, such as typically results from frequently repeated applications, and which prevents rotation of crops sensitive to that herbicide.

Certain herbicides, while not used directly to control weeds in field crops, are used as total vegetation control agents to eliminate weeds entirely in certain right-of-way or industrial situations. However, these herbicides may be deposited by natural means, such as water run-off, onto areas where economically important crops are growing. As a result sensitive field crops may be killed or their growth seriously inhibited. It is therefore highly desirable to be able to modify viable cells to make them resistant to stressful cytotoxic agents.

Isoxaben (-3[1-ethyl-1-methylpropyl]-5-isoxazolyl-2,6, dimethoxybenzamide), 2,6-dichlorobenzonitrile (DCB) and thiazolidinones such as 5-tert-butyl-carbamoyloxy-3-(3-trifluromethyl) phenyl-4-thiazolidnone (TZ), are structurally diverse herbicides. On the basis of biochemical studies of mode of action, their primary target site has been proposed to be the enzyme cellulose synthase, which catalyses the synthesis of cellulose, a major component of plant cell walls. However, the precise target for these herbicides has not been previously described.

Isoxaben (EL-107, Flexidor, Gallery) is a preemergence, broad leaf herbicide used primarily on small grains, turf and ornamentals. The compound is extremely active with an $I_{50}$ for *Brassica napus* of 20 nM (Lefebvre et al., 1987). Isoxaben inhibits the incorporation of glucose into the cellulose-rich, acid-insoluble fraction of isolated walls and is an extremely powerful and specific inhibitor of cell wall biosynthesis (Heim et al., 1990b; Corio-Costet et al., 1991 b). Cell wall-fractionation studies have revealed that the herbicidal action of isoxaben can be explained entirely by its effect on cellulose biosynthesis (Heim et al., 1991). Its probable mode of action is to directly inhibit cellulose synthesis, because resistant cell lines show an unaltered uptake or detoxification of the herbicide (Heim et al., 1991) and only two genetic loci in *Arabidopsis thaliana*, termed ixrA (=ixr1) and ixrB (=ixr2), have been shown to confer resistance (Heim et al., 1989, 1990a). Exhaustive studies have revealed that other cellular processes are unaffected by isoxaben (e.g. seed germination, mitosis, respiration, photosynthesis, and lipid and RNA synthesis, Lefebvre et al., 1987; Corio-Costet et al., 1991a). Treated cells fail to elongate with high fidelity and consequently grow isodiametrically (Lefebvre et al., 1987). This herbicide acts at much lower concentrations (<40x) than dichlobenil, another cellulose synthesis inhibitor (Heim et al., 1990b). Therefore, the properties of isoxaben make it an ideal agent for perturbing the mechanical properties of the primary cell wall.

Thiazolidinones such as 5-tert-butyl-carbamoyloxy-3-(3-trifluromethyl) phenyl-4-thiazolidnone (TZ) are a new class of N-phenyl-lactam-carbamate herbicides (Sharples et al, 1998). TZ shows potential for selective preemergence control of a range of weed species in soybean and other crops. Susceptible weeds include grasses such as *Digitaria* spp., *Setaria* spp., *Sorghum* spp., and small seeded broad leafed weeds which include *Amaranthus* spp., and *Chenopodium* spp. TZ has a similar syndrome of effects on plants as isoxaben. A common mode of action with isoxaben is indicated by the fact that the ixrA1 (=ixr1-1) mutant of *Arabidopsis* exhibits resistance to both isoxaben and TZ (Sharples et al., 1998).

The herbicide 2,6-dichlorobenzonitrile (dichlobenil, DCB) is an effective and specific inhibitor of cellulose synthesis in algae and plants (Delmer et al., 1987). It has been reported to bind to an 18 kd polypeptide in cotton fiber extracts but no mechanism for its action has been demonstrated and no function for the 18 kd protein has been reported.

A crop made more resistant to isoxaben and thiazolidinone herbicides offers a selective means to control and kill weeds without adversely affecting the crop plant. Clearly then, an understanding of the method by which weeds become resistant to herbicides at the molecular level is essential to establishing a basis for the development of sound weed control programs. The molecular basis underlying the expression of isoxaben and thiazolidinone-resistance had remained undetermined until the present invention. Therefore, identification of the mutation site(s) in the CS gene, which code for the mutant plant's isoxaben and thiazolidinone resistance is of agricultural significance. The isolation of a mutant CS gene, which confers resistance to isoxaben and thiazolidinone in higher plants, would provide an opportunity to introduce isoxaben and thiazolidinone resistance into crop plants by genetic engineering. Isoxaben and thiazolidinones, because of their broad-spectrum activity and low mammalian toxicity, are particularly suited as a type of herbicide to which genetically engineered resistance would be economically important in crop plants. The development of isoxaben and thiazolidinone-resistant crops would provide a reliable and cost-effective alternative to conventional weed management programs.

By modifying crop plant cells by the introduction of a functional gene expressing the isoxaben and thiazolidinone-resistant CS enzyme, one can use isoxaben and thiazolidinones or an analogous herbicide with a wide variety of crops at a concentration which ensures the substantially complete or complete removal of weeds, while leaving the crop relatively unaffected. In this manner, substantial economies can be achieved in that fertilizers and water may be more efficiently utilized, and the detrimental effects resulting from the presence of weeds avoided.

The genetic code is degenerate, meaning that more than one codon may be used to encode a particular amino acid, and therefore, the amino acid sequence can be encoded by any set of similar DNA oligonucleotides. With respect to nucleotides, therefore the term "derivative(s)" is intended to encompass those DNA sequences which contain alternative codons which code for the eventual translation of the identical amino acid.

SUMMARY OF THE INVENTION

It is a primary object of this invention to provide isoxaben and thiazolidinone-resistance, nucleic acid sequences encoding isoxaben and thiazolidinone-resistant CS enzymes, constructs containing the genes coding for such isoxaben and thiazolidinone-resistant CS enzymes under the transcriptional and translational control of regulatory genes recognized by a desired host to which the isoxaben and thiazolidinone-resistant CS enzyme genes are foreign, host cells containing such constructs, and organisms and organism parts or products containing such constructs.

It is an additional object of this invention to provide a gene coding for isoxaben and thiazolidinone-resistant CS enzymes useful in the transformation of a crop plant, and thereby effective in the protection of the host cells from the cytotoxic effect of isoxaben and thiazolidinone.

It is also an object of this invention to provide a novel mutant CS gene useful in the transformation of crop plants, wherein the isoxaben and thiazolidinone resistance of the transformed crop plant is greater than that of an untreated isoxaben and thiazolidinone-sensitive wild-type crop plant.

It is a particular object of this invention to provide a novel CS gene capable of coding for sufficient isoxaben and thiazolidinone resistance in a transformed crop plant that, after planting, sufficiently concentrated isoxaben and thiazolidinone herbicide can be applied in a single treatment to the transgenic plant crop to selectively kill substantially all of the weeds, without application of an additional herbicide.

It is further an object of this invention to provide a method of producing a transformed plant crop that, after planting, exhibits greater resistance to isoxaben and thiazolidinone herbicide than that of an isoxaben and thiazolidinone-sensitive wild-type crop plant of the same species.

It is a further object of this invention to increase the effectiveness of isoxaben and thiazolidinone herbicides by producing plant crops less susceptible to damage by these herbicides when used to control weeds.

It is a further object of this invention to provide isoxaben and thiazolidinone-resistant CS enzyme gene constructs useful in selectively distinguishing between host cells containing the construct and host cells lacking such construct.

It is a further object of this invention to provide a method for the rational design of novel chemical compounds that inhibit the activity of plant cellulose synthases and are, therefore, useful as novel herbicides. The knowledge of the site of inhibitory action of the isoxaben and thiazolidinone herbicides disclosed here, in conjunction with knowledge of which amino acid residues can be changed to impart resistance to the inhibitory action of the herbicides enables the design of additional herbicidal compounds by methods familiar to those skilled in the art of rational chemical design.

Another aspect of this invention is an isolated and purified nucleic acid comprising the nucleic acid sequence of (SEQ ID NO: 1).

Another aspect of this invention is an isolated and purified nucleic acid comprising the nucleic acid sequence of (SEQ ID NO: 2).

Another aspect of this invention is the isolated and purified nucleic acids comprising other nucleic acid sequence cited or envisioned by this disclosure.

These and other objects are accomplished pursuant to the practice of this invention.

DESCRIPTION OF THE DRAWINGS

FIG. 1 depicts the relative position of the molecular markers on chromosome V that were used to map the ixr1 gene. Names of BAC-clones are indicated above the line and names of molecular markers are given below the lines. Numbers in brackets are the size of the non-overlapping sequence for each BAC-clone, or the number of recombinants found for each marker

DESCRIPTION OF PREFERRED EMBODIMENTS

Definitions

Before proceeding further with a description of the specific embodiments of the present invention, a number of terms will be defined.

As used herein, a "compound" or "molecule" is an organic or inorganic assembly of atoms of any size, and can include macromolecules, peptides, polypeptides, whole proteins, and polynucleotides.

The determination of percent identity or homology between two sequences is accomplished using the algorithm of Karlin and Altschul (1990) Proc. Nat'l Acad. Sci. USA 87: 2264–2268, modified as in Karlin and Altschul (1993) Proc. Nat'l Acad. Sci. USA 90:5873–5877. Such an algorithm is incorporated into the NBLAST and XBLAST programs of Altschul et al. (1990) J. Mol. Biol. 215:403–410. BLAST nucleotide searches are performed with the NBLAST program, score=100, wordlength=12 to obtain nucleotide sequences homologous to the nucleic acid molecules of the invention. BLAST protein searches are performed with the XBLAST program, score=50, wordlength=3 to obtain amino acid sequences homologous to the protein molecules of the invention. To obtain gapped alignments for comparison purposes, Gapped BLAST is utilized as described in Altschul et al. (1997) Nucleic Acids Res. 25: 3389–3402. When utilizing BLAST and Gapped BLAST programs, the default parameters of the respective programs (e.g., XBLAST and NBLAST) are used. See http://www.ncbi.nlm.nih.gov.

As used herein, a "polynucleotide" is a nucleic acid of more than one nucleotide. A polynucleotide can be made up of multiple poly-nucleotide units that are referred to be description of the unit. For example, a polynucleotide can comprise within its bounds a polynucleotide(s) having a coding sequence(s), a polynucleotide(s) that is a regulatory region(s) and/or other polynucleotide units commonly used in the art.

The isolated nucleic acid molecule of the present invention can include a deoxyribonucleic acid molecule (DNA), such as genomic DNA and complementary cDNA which can be single (coding or noncoding strand) or double stranded, as well as synthetic DNA, such as synthesized single stranded polynucleotide. The isolated nucleic acid molecule of the present invention can also include a ribonucleic acid molecule (RNA).

As used herein, the terms "hybridization" (hybridizing) and "specificity" (specific for) in the context of nucleotide sequences are used interchangeably. The ability of two nucleotide sequences to hybridize to each other is based upon a degree of complementarity of the two nucleotide sequences, which in turn is based on the fraction of matched complementary nucleotide pairs. The more nucleotides is a given sequence that are complementary to another sequence, the greater the degree of hybridization of one to the other. The degree of hybridization also depends on the conditions of stringency which include: temperature, solvent ratios, salt concentrations, and the like.

In particular, "selective hybridization" pertains to conditions in which the degree of hybridization of a polynucleotide of the invention to its target would require complete or nearly complete complementarity. The complementarity must be sufficiently high as to assure that the polynucleotide of the invention will bind specifically to the target relative to binding other nucleic acids present in the hybridization medium. With selective hybridization, complementarity will be 90–100%, preferably 95–100%, more preferably 100%.

The term "stringent conditions" is known in the art from standard protocols (e.g. Current Protocols in Molecular Biology, editors F. Ausubel et al., John Wiley and Sons, Inc. 1994) and is when hybridization to a filter-bound DNA in 0.5M NaHPO.sub4 (pH 7.2), 7% sodium dodecyl sulfate (SDS), 1 mM EDTA at +65° C., and washing in 0.1×SSC/ 0.1% SDS at +68° C.

Degenerate variant is the redunency or degeneracy of the genetic code as is well known in the art. Thus the nucleic acid sequences shown in the sequence listing provided only examples within a larger group of nucleic acids sequences that encode for the polypeptide desired.

"Isolated" nucleic acid will be nucleic acid that is identified and separated from contaminant nucleic acid encoding other polypeptides from the source of nucleic acid. The nucleic acid may be labeled for diagnostic and probe purposes, using any label known and described in the art as useful in connection with diagnostic assays.

Because the genetic code is degenerate, more than one codon may be used to encode a particular amino acid, and therefore, the amino acid sequence can be encoded by any set of similar DNA oligonucleotides. With respect to nucleotides, therefore, the term "derivative(s)" is also intended to encompass those DNA sequences which contain alternative codons which code for the eventual translation of the identical amino acid.

Nucleotide Sequences

The scope of the present invention is not limited to the exact sequence of the cDNA sequences set forth in (SEQ ID NO: 1), (SEQ ID NO:2) and (SEQ ID NO: 3) or the use thereof. The invention contemplates certain modifications to the sequence, including deletions, insertions, and substitutions, that are well known to those skilled in the art. For example, the invention contemplates modifications to the sequence found in (SEQ ID NO: 4) and (SEQ ID NO: 6) that encode the same amino acid substitutions as found in (SEQ ID NO: 1) and (SEQ ID NO: 3). Similarity is expected that other sequence having codons that encode amino acids that are chemically equivalent to the amino acids substituted by (SEQ ID NO: 1) and (SEQ ID NO:2) would have the same resistance effect.

Creating various the point mutation variation envisioned by this invention can be accomplished by a variety of protocols known in the art including those described in U.S. Pat. No. 6,448,048 issued to Tomono et al., on Sep. 20, 2002.

Chemical equivalency can be determined by one or more the following characteristics: charge, size, hydrophobicity/ hydrophilicity, cyclic/non-cyclic, aromatic/non-aromatic etc. For example, a codon encoding a neutral non-polar amino acid can be substituted with another codon that encodes a neutral non-polar amino acid, with a reasonable expectation of producing a biologically equivalent protein.

Amino acids can generally be classified into four groups. Acidic residues are hydrophillic and have a negative charge to loss of H+ at physiological pH. Basic residues are also hydrophillic but have a positive charge to association with H+ at physiological pH. Neutral nonpolar residues are hydrophobic and are not charged at physiological pH. Neutral polar residues are hydrophillic and are not charged at physiological pH. Amino acid residues can be further classified as cyclic or noncyclic and aromatic or nonaromatic, self-explanatory classifications with respect to side chain substituent groups of the residues, and as small or large. The residue is considered small if it contains a total of 4 carbon atoms or less, inclusive of the carboxylcarbon. Small residues are always non-aromatic.

Of naturally occurring amino acids, aspartic acid and glutamic acid are acidic; arginine and lysine are basic and noncylclic; histidine is basic and cyclic; glycine, serine and cysteine are neutral, polar and small; alanine is neutral, nonpolar and small; threonine, asparagine and glutamine are neutral, polar, large and nonaromatic; tyrosine is neutral, polar, large and aromatic; valine, isoleucine, leucine and methionine are neutral, nonpolar, large and nonaromatic; and phenylalanine and tryptophan are neutral, nonpolar, large and aromatic. Proline, although technically neutral, nonpolar, large, cyclic and nonaromatic is a special case due to its known effects on secondary conformation of peptide chains, and is not, therefore included in this defined group.

There are also common amino acids which are not encoded by the genetic code include by example and not limitation: sarcosine, beta-alanine, 2,3 diamino propionic and alpha-aminisobutryric acid which are neutral, nonpolar and small; t-butylalanine, t-butylglycine, -methylisoleucine, norleucine and cyclohexylalanine which are neutral, nonpolar, large and nonaromatic; ornithine which is basic and noncylclic; cysteic acid which is acidic; citrulline acetyl lysine and methionine sufoxide which are neutral, polar, large and nonaromatic; and phenylglycine, 2-napthylalanine, β-2thienylalanine and 1,2,3,4, tetrahydroisoquinoline-3cboxylic acid which are neutral, nonpolar, large and aromatic. Other modifications are known in the art some of which are discussed in U.S. Pat. No. 6,465,237 issued to Tomlinson on Oct. 15, 2002.

This invention embodies the isolation and purification of novel mutant CS genes from isoxaben and thiazolidinone-resistant plants, sequencing to identify the unique mutations, and transforming an isoxaben and thiazolidinone-sensitive plant to confer greater isoxaben and thiazolidinone resistance than that originally possessed by the transformed plant.

The novel CS gene of interest may be obtained from a higher plant, particularly a plant shown capable of resisting isoxaben and thiazolidinone treatment. The mutant plant can be the result of a spontaneous mutation or to various mutagenic processes, including chemical, biological, radioactive, or ultraviolet treatments.

The gene encoding the isoxaben and thiazolidinone-resistance CS enzyme may be cloned by map based cloning, as described herein. As a preferable alternative, the gene encoding the isoxaben and thiazolidinone-resistance CS enzyme may be cloned by using the corresponding gene from *Arabidopsis* or another plant as a heterologous hybridization probe to isolate genomic or cDNA clones of the gene from another plant, or oligonucleotides based on the CS gene nucleotide or polypeptide sequence may be used to isolate all or part of the gene by PCR and these fragments may then be cloned by standard procedures familiar to those skilled in the art.

Depending on the size of the identified fragment, it will usually be further manipulated so that it contains the full coding sequence of the CS gene and its flanking regulatory sequences. Partial cleavage with different restriction enzymes in different reaction mixtures may be employed, followed by cloning of the fragments to determine which of the fragments still retain the ability to provide isoxaben and thiazolidinone-resistant CS activity.

The gene coding for isoxaben and thiazolidinone-resistant CS activity may be modified in a variety of ways, truncating either or both of the 5'- or 3'-termini, extending the 5'- or 3'-termini, or the like. Usually, not more than 25, in particular not more than about 20 codons will be involved in the modification of the naturally occurring isoxaben and thiazolidinone-resistant CS gene. The gene may be extended by as many as 50 amino acids, usually not more than about 30 amino acids. Combinations of substitution, truncation and extension may be employed. Thus the gene may be manipulated in a variety of ways to change the characteristic of the enzyme, for convenience in manipulation of the plasmids, or the like. Based on knowledge of the molecular basis of isoxaben and thiazolidinone-resistance, similar mutations could be introduced by various site directed mutagenesis procedures, or by the production of partially or completely synthetic genes, into other plant CS genes to obtain isoxaben and thiazolidinone-resistance.

The DNA sequence containing the structural gene expressing the isoxaben and thiazolidinone-resistant CS may be joined to a wide variety of other DNA sequences for introduction into an appropriate host cell. The companion sequence will depend upon the nature of the host and the manner of introduction of the DNA sequence into the host.

For prokaryotic hosts, a wide variety of vectors exist which may be used for introduction by transformation, conjugation, transduction or transfection of the DNA sequence into a prokaryotic host. DNA vectors include a wide variety of plasmids, such as pBR322, pMB9, and the like; cosmids, such as pVK100; or viruses, such as P22, and the like.

For eukaryotic hosts, a wide variety of techniques may be employed for DNA introduction into the host, such as transformation with $Ca^{++}$-precipitated DNA, involving a non-replicating DNA sequence, a plasmid or a minichromosome, transformation, microinjection with a micropipette, electroporation, polyethylene glycol (PEG) mediated transformation of protoplasts, or gene gun or particle bombardment techniques. Whether the DNA may be replicated as an episomal element, or whether the DNA may be integrated into the host genome and the structural gene expressed in the host, will be determined by the presence of a competent replication system in the DNA construction. Episomal elements may be employed, such as tumor inducing plasmids, e.g., Ti or Ri, or fragments thereof, or viruses, e.g., CaMV, TMV or fragments thereof, which are not lethal to the host, and where the structural gene is present in such episomal elements in a manner allowing for expression of the structural gene. Of particular interest are fragments having the replication function and lacking other functions such as oncogenesis, virulence, and the like.

To introduce isolated genes or groups of genes into the genome of plant cells an efficient host gene vector system is necessary. The foreign genes should be expressed in the transformed plant cells and stably transmitted, somatically or sexually to a second generation of cells produced. The vector should be capable of introducing, maintaining, and expressing a gene from a variety of sources in the plant cells. Additionally, it should be possible to introduce the vector into a variety of plants, and at a site permitting effective gene expression. Moreover, to be effective, the selected gene must be passed on to progeny by normal reproduction.

The fragments obtained from the isoxaben and thiazolidinone-resistant source may be cloned employing an appropriate cloning vector. Cloning can be carried out in an appropriate unicellular microorganism, e.g., a bacterium, such as *E. coli*, or *Salmonella*. In particular, one may use a phage, where partial or complete digestion provides fragments having about the desired size. For example, the phage lambda may be partially digested with an appropriate restriction enzyme and ligated to fragments resulting from either partial or complete digestion of a plasmid, chromosome, or fragment thereof. Packaging will insure that only fragments of the desired size will be packaged and transduced into the host organism.

The isoxaben and thiazolidinone-resistant CS enzyme may be expressed by any convenient source, either prokaryotic or eukaryotic, including bacteria, yeast, filamentous fungus, animal cells, plant cells, etc. Where secretion is not obtained, the enzyme may be isolated by lysing the cells and isolating the mutant CS according to known ways. Useful ways include chromatography, electrophoresis, affinity chromatography, and the like.

The DNA sequence encoding for the isoxaben and thiazolidinone-resistant CS activity may be used in a variety of ways. The DNA sequence may be used as a probe for the isolation of mutated or wild type CS sequences. Also saturation or site-directed mutagenesis could be performed on a plant CS gene to select for mutants expressing greater levels of herbicide-resistance, as well as resistance to additional classes of herbicide. Alternatively, the DNA sequence may be used for integration by recombination into a host to provide isoxaben and thiazolidinone resistance in the host. The mutant CS gene can also be used as selection marker in the plant transformation experiments using the isoxaben and thiazolidinone herbicide as the selection agent.

With plant cells, the structural gene as part of a construction may be introduced into a plant cell nucleus by micropipette injection for integration by recombination into the host genome. Alternatively, methods including electroporation, polyethylene glycol (PEG) mediated transformation of protoplasts, or gene gun or particle bombardment techniques may be employed for introduction of the structural gene into a plant host cell. Where the structural gene has been obtained from a source having regulatory signals, which are not recognized by the plant host, it may be necessary to introduce the appropriate regulatory signals for expression. Where a virus or plasmid, e.g., tumor inducing plasmid, is employed and has been mapped, a restriction site can be chosen which is downstream from a promoter into which the structural gene may be inserted at the appropriate distance from the promoter. Where the DNA sequences do not provide an appropriate restriction site, one can digest for various times with an exonuclease, such as Bal31 and insert a synthetic restriction endonuclease site (linker).

Directed genetic modification and expression of foreign genes in dicotyledons (broad-leaf plants) such as tobacco, *Arabidopsis* etc. has been shown to be possible using the T-DNA of the Ti plasmid of *Agrobacterium tumefaciens*. Following genetically engineered insertion of a foreign DNA fragment into T-DNA in *Agrobacterium*, the host plant can be transfected by the bacterium or Ti plasmid, thus inserting the foreign DNA into the host plant chromosome to eventually produce a genetically engineered plant. Alternatively Ri, or root-inducing, plasmids may be used as the gene vectors. Although *Agrobacterium* effectively transform only dicots, the Ti plasmid permits the efficacious manipulation of the bacteria to act as vectors in monocotyledonous crop plants, i.e., wheat, barley, rice, rye, etc. Alternatively, Ti plasmids or other plasmids may be introduced into the monocots by artificial methods such as microinjection, or fusion between the monocot protoplasts and bacterial spheroplasts containing the T-region which could then be integrated into the plant nuclear DNA.

By employing the T-DNA right border, or both borders, where the borders flank an expression cassette comprising the isoxaben and thiazolidinone-resistant CS structural gene under transcriptional and translational regulatory signals for initiation and termination recognized by the plant host, the expression cassette may be integrated into the plant genome and provide for expression of the isoxaben and thiazolidinone-resistant CS enzyme in the plant cell at various stages of differentiation. Various constructs can be prepared providing for expression in plant cells.

To provide for transcription, a variety of transcriptional initiation regions (promoter regions), either constitutive or inducible, may be employed. The transcriptional initiation region is joined to the structural gene encoding the isoxaben and thiazolidinone-resistant CS activity to provide for transcriptional initiation upstream from the initiation codon, normally within about 200 bases of the initiation codon, where the untranslated 5'-region lacks an ATG. The 3'-end of the structural gene will have one or more stop codons which will be joined to a transcriptional termination region functional in a plant host, which termination region may be associated with the same or different structural gene as the initiation region.

The expression cassette is characterized by having the initiation region, the structural gene under the transcriptional control of the initiation region, and the termination region providing for termination of transcription and processing of the messenger RNA, in the direction of transcription as appropriate.

Transcriptional and translational regulatory regions, conveniently tml promoter and terminator regions from *A. tumefaciens* may be employed, which allow for constitutive expression of the isoxaben and thiazolidinone-resistant CS gene. Alternatively, other promoters and/or terminators may be employed, particularly promoters which provide for inducible expression or regulated expression in a plant host. Promoter regions which may be used from the Ti-plasmid include opine promoters, such as the octopine synthase promoter, nopaline synthase promoter, agropine synthase promoter, mannopine synthase promoter, or the like. Other promoters include viral promoters, such as CaMV Region VI promoter or full length (35S) promoter or the like.

The various sequences may be joined together in conventional ways. The promoter region may be identified by the region being 5' from the structural gene, for example, the tml gene, and may be selected and isolated by restriction mapping and sequencing. Similarly, the terminator region may be isolated as the region 3' from the structural gene. The sequences may be cloned and joined in the proper orientation to provide for constitutive expression of the isoxaben and thiazolidinone-resistant CS gene in a plant host.

The expression cassette expressing the isoxaben and thiazolidinone-resistant CS enzyme may be introduced into a wide variety of plants, both monocotyledon and dicotyledon, including maize, wheat, soybean, tobacco, cotton, tomatoes, potatoes, *Brassica* species, rice, peanuts, petunia, sunflower, sugar beet, turfgrass, etc. The gene may be present in cells or plant parts including callus, tissue, roots, tubers, propagules, plantlets, seeds leaves, seedlings, pollen, or the like.

By providing for isoxaben and thiazolidinone-resistant plants, a wide variety of formulations may be employed for protecting crops from weeds, so as to enhance crop growth and reduce competition for nutrients. The mutant CS gene can be introduced into plants and regenerated to produce a new family of transgenic plants, which possess increased resistance to isoxaben and thiazolidinone as compared with that possessed by the corresponding wild plants. Isoxaben or a thiazolidinone could be used by itself for postemergence control of weeds with transgenically protected crops, such as sunflower, soybeans, corn, cotton, etc., or alternatively, in combination formulations with other products.

Formulations could include other additives, such as detergents, adjuvants, spreading agents, sticking agents, stabilizing agents, or the like. The formulations may either be wet or dry preparations, including flowable powders, emulsifiable concentrates and liquid concentrates, such as are known in the art. The herbicidal solutions may be applied in accordance with conventional methods, for example, by spraying, irrigation, dusting, or the like.

The following is further exemplary of the invention, and specifically defines preferred techniques for the production of an isoxaben and thiazolidinone herbicide resistant *Arabidopsis thaliana*, cellulose synthase gene, a process for conferring isoxaben and thiazolidinone herbicide resistance to plants other than *Arabidopsis thaliana*, and isoxaben and thiazolidinone herbicide resistant transgenic plants. The following examples are offered by way of illustration and not by way of limitation.

EXAMPLES AND MATERIALS AND METHODS

1. Plant and Seed Material.

Seeds from homozygous isoxaben-resistant mutants ixr1-1 (DH47) and ixr1-2 (DH48) (Heim et al., 1989) were obtained from the *Arabidopsis* Biological Resource Center, Columbus, Ohio (ABRC stock numbers CS 6201 and CS 6202). Seeds were vernalized for five days in 0.15% water agar at 6° C. prior to planting in a commercial peat-vermiculite-perlite mix (ProMix HP with a 1 cm top-layer of ProMix PGX, Premier Horticulture Inc., Red Hill, Pa., Canada). Plants were grown in the greenhouses of Carnegie Institution of Washington, Department of Plant Biology, Stanford, Calif. between July 1998 and June 1999. Seeds from self-pollinated ixr1-1 and ixr1-2 mutants were collected separately and used for further experiments.

2. Isoxaben-Resistance Pilot Screen.

Isoxaben (95%, N-3-[1-ethyl-1-methyl-propyl]-5-isoxazolyl-2, 6-dimethoxybenzamide) was graciously supplied by DowElanco (Indianapolis, Ind.) and was made up as a concentrated dimethylsulfoxide (DMSO) stock solution and used at concentrations ranging from 0.03 to 10.0 µM. The final concentration of DMSO was always 0.025%. Control cultures without isoxaben contained the same amount of DMSO as the isoxaben-treated cultures; no effect of DMSO was noted.

In order to determine a useful isoxaben concentration, which makes it possible to clearly distinguish ixr1-1-, ixr1-2- and wild-type *Arabidopsis* plants in our growth-conditions, seeds of the different genotypes were treated and plants grown as above and sprayed every 3 days, starting at the seedling stage, with 1 ml/6 cm² soil surface 0.1, 0.3, 1.0 or 3.0 µM isoxaben dissolved in water containing 0.025% (v/v) dimethylsulfoxide. This experiment showed that a concentration of 1.0–3.0 µM isoxaben in the application solution is high enough to readily allow discrimination of resistant and susceptible plants.

3. Genetic Crosses.

Young flowers of isoxaben-resistant ixr1-1 and ixr1-2 mutant plants were carefully emasculated (removal of all six immature stamens) to prevent self-pollination of these flowers. After two days non-aborted, stamen-less flowers were cross-pollinated with mature pollen from *Arabidopsis thaliana* Landsberg erecta (Ler) wild-type. F1-seeds from each mature dry silique were carefully collected, vernalized and planted as described above and the F1-plants grown and allowed to self-pollinate. F2-seeds from each ixr1×Ler F1-plant were collected separately.

4. Growth Analyses of F1- and F2-Plants.

Seeds from wild-type Col and Ler, ixr1-1 and ixr1-2 homozygous mutants and F1- and F2-seeds were germinated again and treated as described using 2.0 µM isoxaben in the solution. Wild-type plants didn't grow at all, homozygous mutants grew well (ixr1-1 grew better than ixr1-2). All heterozygous mutant F1-plants had clearly reduced growth as compared to the homozygous mutants and F2-plants from the ixr1-2×wild-type Ler showed a clear 1:2:1 segregation, as expected, in their growth behavior.

5. Growth of the Mapping Population.

Due to the clear growth segregation pattern of F2-plants from the ixr1-2×wild-type Ler cross after treatment with 2.0 µM isoxaben, approximately 102 mg of these F2-seeds (ca. 5000 seeds) were planted in 80 150 cm² pots (60–65 seeds per pot). An average of 14–16 well growing plants were obtained after 2.0 µM isoxaben-treatment, fitting precisely with the expected number of F2-plants homozygous for the ixr1 locus. 1056 (11×96) of these plants were labeled and all other plants removed from the pots. After the plants started to bolt, tissue samples (one small cauline leaf or one small inflorescence per plant) were collected in 96-well PCR-plates (MJ Research, Cambridge, Mass.) and stored at −20° C. until use for DNA-preparation. From all recombinant plants (see below) a second tissue sample (young leaves and flower buds) was collected one week later as a back-up and to prepare higher quality CTAB-DNA.

6. Genomic DNA-Preparation.

Alkaline Lysis protocol (Klimyuk et al., 1993): 50 µl 0.25 N NaOH were added to each of the 1056 plant tissue samples collected in 96-well PCR plates (see above) on ice, and up to nine samples simultaneously ground with the upper end of polyethylene stirring rods (Sarstedt, Nümbrecht, Germany). After heating the samples in a thermocycler (model PTC-100, MJ Research) for 30 sec at 96° C., 50 µl of 0.25 N HCl and 25 µl 0.5 M Tris-HCl (pH 8.0), 0.25% Nonidet P-40 were added and again heated to 96° C. for two minutes. Afterwards the samples were directly used for PCR with SSLP-markers or stored at −20° C. until use.

CTAB-protocol: 400 µl 2×CTAB-buffer (2% (w/v) cetyl-trimethyl-ammonium bromide, 100 mM Tris-HCl pH 8.0, 20 mM EDTA, 1.4 M NaCl, 1% (w/v) polyvinyl-pyrrolidone (MW 40,000) were added to approx. 50 mg, in liquid nitrogen crushed, plant-material, mixed and incubated for 30–60 min at 65° C. 400 µl chloroform were added, the mixture vigorously mixed during 15 sec and then spun for 10 min, at 13,000×g. The clear supernatant was carefully removed, transferred to a new sterile microtube and the DNA precipitated by addition of one volume 95% ice-cold isopropanol. After one hour at −20° C. the DNA was pelleted by centrifugation at 13,000×g, 10 min. The supernatant was removed and the pellet washed with 70% ice-cold ethanol and allowed to dry at room temperature. The DNA-pellet was dissolved in 100 µl 10 mM Tris-HCl pH 8.0, 1 mM EDTA and the DNA-concentration determined.

7. Genetic Mapping of the ixr1 Locus.

Heim et al., (1989) mapped the ixr1 locus with phenotypic markers to the top arm of chromosome V of the *Arabidopsis* genome, approximately 3 cMorgan from the marker lutescens. Using southern blotting with restriction fragment length polymorphism (RFLP) markers the locus was subsequently mapped between chromosome V RFLP-markers g3715 and m217, approximately 3.7 cMorgan proximal to the former and 1.5 cMorgan distal to the latter© Somerville, unpublished). Using the chromosome V sequence information from the public Kasuza *Arabidopsis* data base and the RFLP-mapping data, the following two simple sequence length polymorphism (SSLP) markers were generated close to g3715 and m217.

SSLP-marker med24.2 (approx. 300 kb proximal of g3715 on the physical map of chromosome V, is directed against a $(TG)_{13}$ dinucleotide repeat on chromosome V BAC-clone MED24. Two oligonucleotide primers (F: 5' CGAACTTGAGACCTCTTGA 3' (SEQ ID NO:7); R: 5' GCTTACCTGGAGACAGTCA 3' (SEQ ID NO: 8)) were designed with the Oligo Primer Analysis Software, version 5.0 (National Biosciences, Plymouth, Minn.) to PCR-amplify a 124 bp fragment from genomic wild-type Columbia DNA, containing the $(TG)_{13}$ dinucleotide repeat. Using the same primers a shorter PCR-product (<120 bp) is obtained from wild-type Landsberg genomic DNA, whereas a Col×

Ler heterozygous plant gives both products, as can be easily seen on 4% agarose-gels. PCR-conditions for SSLP-marker med24.2:50 mM KCl, 10 mM Tris-HCl (pH 9.0@25° C.), 0.1% Triton X-100, 200 μM dATP, dGTP, dTTP, dCTP (each), 5 pmoles primer F, 5 pmoles primer R, 2.0 mM MgCl$_2$, 1.0 Units Taq. Polymerase (Promega, Madison, Wis.), 10–50 ng genomic DNA, final volume 20 μl. PCR-program: 1 min 94° C.; 40 cycles (20 sec 94° C., 20 sec 55° C., 40 sec 72° C.), 3 min 72° C.

SSLP-marker moj9.2 (approx. 100 kb proximal of m217 on the physical map of chromosome V;

| | |
|---|---|
| molecular target: | (TA)$_{19}$ dinucleotide repeat (bases 53618–53655) on chromosome V BAC-clone MOJ9 |
| PCR primers: | F: 5' CATGATCCATCGTCTTAGT 3' (SEQ ID NO: 9); R: 5' AATATCGCTTGTTTTTGC 3' (SEQ ID NO: 10) |
| PCR-product size: | 179 bp in Col, ca.160 bp in Ler |
| PCR-conditions: | as for med24.2 with 2.2 mM MgCl$_2$. |

In all 1056 plants (=2112 chromosomes) 52 recombinants (heterozygotes for the marker) were found for med24.2 placing it 2.46 cMorgan north of ixr1 on the genetic map of chromosome V. For the SSLP-marker moj9.2 39 recombinants were found in 2112 chromosome placing this marker 1.85 cMorgan south of ixr1. The DNA of one plant was recombinant for both markers. New tissue samples from all 90 recombinants were collected and genomic DNA prepared using the CTAB-protocol (see above). These higher quality DNA-preparations were subsequently used for mapping of the ixr1-locus with six closer markers (see FIG. 1), two additional SSLP-markers muk11.1 and k18i23.1, that were identified for the purpose, and the published SSLP-markers nga158 and nga225 (Bell et al, 1994), as well as the cleaved amplified polymorphic sequence (CAPS) marker PAI2 (Bender and Fink 1995) and a CAPS-marker named MUG13E, that was identified for the purpose.

SSLP-marker muk11.1 (approx. 500 kb proximal of med24.2 on the physical map of chromosome V.

| | |
|---|---|
| molecular target: | (GA)$_{38}$ dinucleotide repeat (bases 57187–57252) on chromosome V BAC-clone MUK11 |
| PCR primers: | F: 5' TCCAAAGCTAAATCGCTAT 3' (SEQ ID NO: 11) R: 5' CTCCGTCTATTCAAGATGC 3' (SEQ ID NO: 12) |
| PCR-product size: | 177 bp in Col, ca.120 bp in Ler |
| PCR-conditions: | as for med24.2 |

SSLP-marker nga158 (approx. 500 kb distal of moj9.2 on the physical map of chromosome V.

| | |
|---|---|
| molecular target: | (CT)$_{14}$ dinucleotide repeat (bases 19384–19411) on BAC-clone MJJ3 |
| PCR primers: | F: 5' ACCTGAACCATCCTCCGTC 3' (SEQ ID NO: 13) R: 5' TCATTTTGGCCGACTTAGC 3' (SEQ ID NO: 14) |
| PCR-product size: | 108 bp in Col, 104 bp in Ler |
| PCR-conditions: | as for med24.2, except that the annealing temperature in the PCR was raised to 60° C. |

After this first round of convergence 13 recombinants remained on the distal side and 11 recombinants remained on the proximal side of the ixr1-locus. The earlier mentioned double-recombinant was not heterozygous for nga158.

SSLP-marker nga225 (approx. 36 kb proximal of muk11.1 on the sequencing map of chromosome V.

| | |
|---|---|
| molecular target: | imperfect (GA)$_{21}$ dinucleotide repeat (bases 12203–12244) on chromosome V BAC-clone MUG13 |
| PCR primers: | F: 5' TCTCCCCACTAGTTTTGTGTCC 3' (SEQ ID NO: 15) R: 5' GAAATCCAAATCCCAGAGAGG 3' (SEQ ID NO: 16) |
| PCR-product size: | 119 bp in Col, 189 bp in Ler. |
| PCR-conditions: | as for med24.2, except that MgCl$_2$ was 1.75 mM. |

CAPS-marker MUG13E (approx. 60 kb proximal of nga225, on the right end of BAC-clone MUG13 on the sequencing map of chromosome V.

| | |
|---|---|
| molecular target: | AccI restriction enzyme site, which is present in the sequence of ecotype Landsberg erecta, but not Columbia. |
| PCR primers: | F: 5' GATTTCCCCAGACGATTT 3' (SEQ ID NO: 17) R: 5' AGTTTATTTGTTGCGGTTTT 3' (SEQ ID NO: 18) |
| PCR-product size: | 2033 bp fragment (bases 79,441–81,473 of BAC MUG13) in Col and Ler before AccI-digest. 1228 and 805 bp fragments in Ler after digest. |
| PCR-conditions: | as for PAI2-marker, but annealing temperature was 54° C. |
| AccI-digest: | 7 μl of PCR-product were mixed with 9 μl H2O, 2 μl 10× buffer M (Amersham), 2 μl BSA (1 mg/ml) and 1U AccI, and digested for 5 hrs at 37° C. 10 μl of each digest were analyzed on a 1.2% agarose gel. |

CAPS-marker PAI2 (approx. 33 kb distal of nga158 on the physical map of chromosome V.

| | |
|---|---|
| molecular target: | AflIII restriction enzyme site, which is present in PAI2-gene from ecotype Columbia, but not Landsberg erecta. |
| PCR primers: | F: 5' CAGTTAATGAAACAAGCTTTGTTC 3' (SEQ ID NO: 19) R: 5' GTTGAGAAAATCACTTTGGTG 3' (SEQ ID NO: 20) |
| PCR-product size: | 645 bp fragment (bases 45928–46572 on BAC clone MOP10) in Col and Ler before AflIII-digest. 590 and 55 bp fragments in Col after digest. |
| PCR-conditions: | 50 mM KCl, 10 mM Tris-HCl (pH 9.0 @ 25° C.), 0.1% Triton? X-100, 250 μM dATP, dGTP, dTTP, dCTP (each), 5 pmoles primer F, 5 pmoles primer R, 2.5 mM MgCl$_2$, 1.0 Units Taq. Polymerase (Promega), 40–50 ng genomic DNA, final volume 25 μl. PCR-program: 1 min 94° C.; 35 cycles (20 sec 94° C., 20 sec 58° C., 90 sec 72° C.), 3 min 72° C. |
| AflIII-digest: | 7 μl of PCR-product were mixed with 9 μl H2O, 2 μl 10× buffer H (Amersham), 2 μl BSA (1 mg/ml) and 1U AflIII, and digested for 5 hrs at 37° C. 10 μl of each digest were analyzed on a 2.5% agarose gel. |

SSLP-marker k18i23.1 (approx. 101 kb proximal of PAI2 on the sequencing map of chr, V.

| | |
|---|---|
| molecular target: | purine-rich stretch (bases 17830–17870) on chromosome V BAC-clone K18I23. Length polymorphism was detected by comparative sequencing of the Ler and Col genomic sequence of that region. |

| | |
|---|---|
| PCR primers: | F: 5' TGGTTAGATTTGCTGTT 3'<br>(SEQ ID NO: 21)<br>R: 5' ATTCTGCATTATTAGTTGTC 3'<br>(SEQ ID NO: 22) |
| PCR-product size: | 139 bp in Col, 133 bp in Ler |
| PCR-conditions: | as for med24.2, except that MgCl$_2$ was 2.5 mM and the annealing temperature during PCR was lowered to 48° C. |

After convergence with these four markers three recombinants remained on the distal side and another three recombinants remained on the proximal side of the ixr1-locus. The region between MUG13E and k18i23.1 is approx. 53 kb in size and is spanned by three BAC-clones (MUG13, K2A11, K18123). Proximal of MUG13E there are no predicted genes left on BAC-clone MUG13. Distal of k18i23.1 on annotated BAC-clone K18123 there are no obvious candidate genes that explain the resistance of the ixr1-mutants towards the cellulose biosynthesis inhibitor isoxaben. However, A BLAST-N search of the small not annotated (as of Aug. 14, 1999) BAC K2A11 (29.3 kb, GENBANK accession #AB018111 (SEQ ID NO: 23)) revealed a gene with perfect identity of its exons (as predicted by GRAIL, GENSCAN 1.0 and NetPlantGene) to the Ath-B-mRNA (GENBANK accession #AF027174 (SEQ ID NO: 24), which encodes a cellulose synthase. It is therefore concluded that the genomic cellulose synthase sequence on BAC-clone K2A11 encodes the Ath-B mRNA.

Amplification and Sequencing of the Cellulose Synthase Gene from Wild-Type Columbia, ixr1-1 and ixr1-2 Mutant Genomic DNA Genomic DNA for each genotype was prepared from a mixture of young growing leaves and inflorescence tissue using the CTAB-protocol (see above). Six oligonucleotide primers were then designed (Oligo Primer Analysis Software, version 5.0) to amplify three (A, B, C) overlapping PCR-fragments, spanning the entire coding sequence of this cellulose synthase gene on BAC-clone K2A11 (see FIG. 2).

| | |
|---|---|
| Fragment A | was amplified with primers<br>F$_a$ (5'-TTAGCCATCCCAAGATTCT-3') (SEQ ID NO: 25)<br>and<br>R$_a$ (5'-CTTCAAGGGGTCAACAGTA-3') (SEQ ID NO: 26)<br>giving a 2034 bp PCR-product (bases 13939–15972 on K2A11). |
| Fragment B | F$_b$ (5'-TACCGAGCGTTTTTCCTAT-3') (SEQ ID NO: 27)<br>R$_b$ (5'-CCAGCACCTAAGTTTCACA-3') (SEQ ID NO: 28)<br>2064 bp PCR-product (bases 12382–14445 on K2A11). |
| Fragment C | F$_c$ (5'-GTTCAGTTCCCACAAAGATT-3')<br>(SEQ ID NO: 29)<br>R$_c$ (5'-TCATTCCGACCAAAAGTT-3') (SEQ ID NO: 30)<br>2395 bp PCR-product (bases 10620–13014 on K2A11). |

PCR-conditions: 50 mM KCl, 10 mM Tris-HCl (pH 9.0@ 25° C.), 0.1% Triton? X-100, 250 µM dATP, dGTP, dTTP, dCTP (each), 10 pmoles primer F$_{a,b,c}$, 10 pmoles primer R$_{a,b,c}$, 2.5 mM MgCl$_2$, 2.0 Units Taq. Polymerase (Promega), 0.2 Units proofreading Pfu-Polymerase, 70–80 ng genomic DNA, final volume 50 µl. PCR-program: 1 min 94° C.; 35 cycles (20 sec 94° C., 20 sec 55° C., 2 min 72° C.), 3 min 72° C. Although a proofreading Pfu-Polymerase was added in the PCR, the fragments, which revealed the ixr1-1 and ixr1-2 point-mutations were amplified two more times and re-sequenced with the appropriate primers (see FIG. 2, primers F10, R9, R10) to demonstrate that the mutations were not due to misincorporation of a dNTP during early cycles of PCR.

50 µl PCR-product were mixed with 10 µl 6× loading dye and loaded on a 1.2% agarose gel. All reactions yielded just one ethidium-bromide stained band when visualized under UV-light. These bands were cut out and the gel slices transferred in a microcolumn (Wizard miniprep, Promega) and spun 5 min at 8,000×g and 5 min at 13,000×g. The eluate was collected in a microtube and the residual in the gel slice remaining DNA was isolated using the QIAEX-kit (QIAGEN, Hilden, Germany). The collected DNA was then precipitated at −20° C. after adding 20 µg glycogen, 300 mM sodium-acetate pH 5.0 and 45% isopropanol. After one hour the DNA was pelleted by centrifugation at 13,000×g for 10 min. The supernatant was removed and the pellet washed briefly with 70% ice-cold ethanol and allowed to dry at room temperature. Finally the DNA-pellet was dissolved in 50 µl 10 mM Tris-HCl pH 8.0, 0.1 mM EDTA and the DNA-concentration determined.

20 sequencing primers (F1–F10, R1–R10, 18–21-mers) were designed (Oligo Primer Analysis Software, version 5.0) equally spread over both strands in the coding region of the candidate cellulose synthase gene (see FIG. 2). Sequencing reactions were set up by mixing 8 µl Big-Dye™ Dideoxy-terminator reaction-mix (PE-Applied Biosystems, Foster City, Calif.), 3.2 pmoles sequencing primer and 70–90 ng of the appropriate gene-cleaned PCR-product in a final volume of 20 µl. PCR-program: 1 min 94° C.; 25 cycles (20 sec 94° C., 20 sec 50/55/58° C. (depending on the sequencing primer), 4 min 60° C.). 20 µl 2 mM MgCl$_2$ and 55 µl 95% ethanol were then added to each 20 µl sequencing reaction and the ssDNA allowed to precipitate for 30–60 min at room temperature. After centrifugation (13,000×g, 15 min) the supernatant was quantitatively removed, the tubes with the lids open allowed to dry and the ssDNA dissolved in 20 µl template suppression reagent (PE-Applied Biosystems), incubated 10 min at 65° C., carefully vortexed, denatured 2 min at 94° C. and then stored on ice until injection in an ABI 377 automated sequencer (PE-Applied Biosystems). Sequence files were analyzed using the ABI-Prism Sequence Navigator and Sequence Analysis software (PE-Applied Biosystems).

Results

The homozygous ixr1-1 and ixr1-2 mutant plants are 300 and 90 times, respectively, more resistant to isoxaben than wild type plants (Heim et al., 1989). ixr1-1 (ixr1-2 was not tested) is also more resistant to a new thiazolidinone herbicide (TZ, compound 1). At 12 µM the thiazolidinone herbicide kills wild type *Arabidopsis*, but reduces growth of the ixr1-1 mutant by only 50% (Sharples et al., 1998).

The ixr1-2 mutation was mapped with high resolution to a small region on the top arm of chromosome V as described in materials and methods. The mapping results indicated that the ixr1 mutations mapped very near to a gene, Ath-B, encoding cellulose synthase. A cDNA clone for the Ath-B mRNA has previously been described by Arioli et al. (1998). The nucleotide-sequence of this clone and the deduced amino acid sequence were deposited in GenBank as accession number AF027174 (SEQ ID NO: 24). Comparison of the sequence of the cDNA to the genomic sequence present on BAC clone K2A11 (GenBank accession number AB018111 (SEQ ID NO: 23) indicates that the cDNA clone has 87 nucleotides at the 5' end that are not present in the genomic sequence. This extra sequence corresponds to a 59 nucleotide multiple cloning site (G GACTC GCGCGC CTGCAG GTCGAC ACTAGT GGATCC AAA GAATTC G CGGCCG C GTCGAC (SEQ ID NO: 31), restriction enzyme sites are shown in italics) that was introduced during cloning of the cDNA and an additional 28 nucleotide fragment of DNA (TACGGCTGCGAGMGACGACA-GAAGGGG) (SEQ ID NO: 32) that was also introduced at some stage during the cloning of the cDNA (see bottom middle insert in FIG. 2). A search of GenBank indicated that this sequence is also found at the 5' ends of other cDNA clones; thus it is a common artifact in some libraries.

The first nucleotide of the mRNA that corresponds to the genomic clone is nucleotide 15966 of BAC K2A11 (GenBank accession number AB018111)(SEQ ID NO: 23). The open reading frame of the gene begins at nucleotide 15688 (start codon) of BAC K2A11 and ends at nucleotide 10999 (stop codon). The genomic clone contains an intron in the 5' non-translated leader sequence that corresponds to nucleotides 15736 to 15845 of BAC K2A11 and another 13 introns which divide the coding sequence in 14 exons (FIG. 2), as predicted by GRAIL, GENSCAN 1.0 and NetPlant-Gene splice-site/exon-intron analysis. The positions of the introns and exons in the coding sequence are listed in Table 1.

In view of the evidence indicating that the mechanism of action of the isoxaben and thiazolidinone herbicides is to inhibit cellulose synthesis, this observation suggested that Ath-B might encode the ixr1 gene. To test this hypothesis, the Ath-B gene was cloned and sequenced from Columbia wild type and from the ixr1-1 and ixr1-2 mutants. This revealed that the Ath-B gene from the ixr1-1 mutant was identical to the wild type except for a G to A change at nucleotide 11204 on the coding (minus) strand of BAC K2A11. This mutation leads to replacement of a conserved glycine at position 998 in the Ath-B protein (GenBank accession number AF027174)(SEQ ID NO: 24) with an aspartic acid residue. Comparison of the nucleotide sequence of the Ath-B gene from wild type and the ixr1-2 mutant indicated that they were identical except for a C to T change at nucleotide 11372 on the coding (minus) strand of BAC K2A11. This mutation resulted in replacement of a conserved threonine residue at position 942 in the Ath-B protein with an isoleucine residue. Thus, both of the ixr1 mutations occurred in exon 14 (FIG. 2). We conclude that the Ath-B gene and the IXR1 gene are identical and henceforth refer to the gene as IXR1.

This result teaches that either of two amino acid changes in the IXR1 gene renders the corresponding enzyme resistant to the inhibitory activity of the isoxaben and thiazolidinone herbicides. This invention has utility in a number of different ways.

Many plants are killed or injured by exposure to isoxaben and thiazolidinone herbicides. In order to render these plants resistant to these herbicides it is possible to introduce the herbicide resistant forms of the IXR1 gene described herein into susceptible plants in such a way that the gene is stably inherited and expressed at a sufficient level so that it confers resistance to the herbicides. Plants can be obtained which are isoxaben and thiazolidinone-resistant and can be grown in the field in the presence of isoxaben and thiazolidinone without significant adverse effect on their growth.

In addition to directly using the modified genes described herein, it is possible to create similarly modified forms of the gene from other species so that these genes have equivalent utility. Thus, the IXR1 gene could be cloned from another plant by any of the methods commonly used to isolate orthologous genes from distantly related plant species. The mutations corresponding to those described herein could then be introduced into these orthologs and the modified orthologs then used to confer isoxaben and thiazolidinone resistance. This mutant gene can also be used as a selection marker in plant transformation systems with its native promoter in dicots and with a modified promoter in monocots. The exact method used to introduce the gene into a particular species of plant will vary from one species to another.

An important use of the subject invention is to facilitate the design of novel herbicides that act on cellulose synthase. One kind of application, in this respect, is to use computer programs to model the secondary, tertiary and quaternary structure of the IXR1 wild type and mutant proteins based on the amino acid sequences of the gene products. By using such computer programs it is possible to model how the known isoxaben and thiazolidinone herbicides interact with the protein and also to model why the mutations revealed herein provide resistance to these and related compounds. This knowledge may be used to design variants of known herbicides that are active at lower rates of application or have other useful properties such as high rate of uptake by the plant, low non-plant toxicity, rapid turnover in soil or any number of other qualities that are associated with the most useful herbicides. By comparing the known or predicted structures of the IXR1 gene from many different plant species, it may be possible to develop an understanding of how to design novel chemical inhibitors that would have broad or narrow specificity for certain classes of plants.

A related approach is to directly obtain the higher order structure of the IXR1 protein. Because the IXR1 protein is thought to be membrane associated, it may be technically challenging to obtain high resolution structural information by methods such as X-ray crystallography. However, because of parallel advances in analytical methods such as NMR, it may eventually be possible to obtain a higher order structure for use in such purposes. The IXR1 gene could be expressed in various alternative hosts systems in conjunction with site-directed mutagenesis to study the mechanisms by which different groups of herbicides inhibit CS. Alternatively, the system could be used to characterize the sites involved in regulation, catalysis, and herbicide binding. Binding studies may be possible on polypeptide subfragments of the protein and may not depend on the protein having overall catalytic activity.

Although the foregoing invention has been described in some detail by way of illustration and example for purposes of clarity and understanding, it will be obvious that certain changes and modifications may be practiced within the scope of the appended claims without departing from the spirit and scope of the invention.

Having described the basic concept of the invention, it will be apparent to those skilled in the art that the foregoing detailed disclosure is intended to be presented by way of example only, and is not limiting. Various alterations, improvements, and modifications are intended to be suggested and are within the scope and spirit of the present invention. Additionally, the recited order of the elements or sequences, or the use of numbers, letters or other designations therefor, is not intended to limit the claimed processes to any order except as may be specified in the claims. Accordingly, the invention is limited only by the following claims and equivalents thereto.

All publications and patent documents cited in this application are incorporated by reference in their entirety for all purposes to the same extent as if each individual publication or patent document were so individually denoted.

TABLE 1

Positions on BAC K2A11 and sizes of introns and coding exons of IXR1 in the coding region, as predicted by GRAIL, GENSCAN 1.0 and NetPlantGene. The positions of the first and last nucleotide of the start and stop codon, respectively, are shown in bold.

| | Exon | | Intron | |
|---|---|---|---|---|
| # | position on K2A11 | size (nt) | position on K2A11 | size (nt) |
| 1 | 15688–15665 | 24 | 15664–15493 | 172 |
| 2 | 15492–15297 | 196 | 15296–15179 | 118 |
| 3 | 15178–14973 | 206 | 14972–14880 | 93 |
| 4 | 14879–14777 | 103 | 14776–14665 | 112 |
| 5 | 14664–14487 | 178 | 14486–14379 | 118 |
| 6 | 14378–14112 | 267 | 14111–14012 | 100 |
| 7 | 14011–13666 | 346 | 13665–13586 | 80 |
| 8 | 13585–13448 | 138 | 13447–13360 | 88 |
| 9 | 13359–13234 | 126 | 13233–13153 | 81 |
| 10 | 13152–12940 | 213 | 12939–12814 | 126 |
| 11 | 12813–12552 | 262 | 12551–12389 | 163 |
| 12 | 12388–12186 | 203 | 12185–12090 | 96 |
| 13 | 12089–11739 | 351 | 11738–11584 | 155 |
| 14 | 11583–10999 | 585 | | |

REFERENCES

Arioli, T., Peng, L., Betzner, A. S., Burn, J., Wittke, W., Herth, W., Camilleri, C., Höfte, H., Plazinski, J., Birch, R. Cork, A., Glover, J., Redmond, J., and Williamson, R. E. 1998. Molecular analysis of cellulose biosynthesis in *Arabidopsis*. *Science* 279, 717–720.

Bell, C. J. and Ecker, J. R. (1994) Assignment of 30 microsatellite loci to the linkage map of *Arabidopsis*. *Genomics* 19, 137–144.

Bender, J. and Fink, G. R. (1995) Epigenetic control of an endogenous gene family Is revealed by a novel blue fluorescent mutant of *Arabidopsis*. *Cell* 83, 725–734.

Corio-Costet, M.-F., Agnese, M. D., Scalla, R. (1991a) Effects of isoxaben on sensitive and tolerant plant cell cultures. I. Metabolic fate of isoxaben. *Pestic. Biochem. Physiol.* 40, 246–254.

Corio-Costet, M.-F., Lherminier, J., Scalla, R. (1991b) Effect of isoxaben on sensitive and tolerant plant cell cultures. II. Cellular alterations and inhibition of the synthesis of acid-insoluble cell wall material. *Pestic. Biochem. Physiol.* 40, 255–265.

Delmer, D. P., Amor, Y. (1995) Cellulose biosynthesis. *Plant Cell* 7, 987–1000.

Delmer, D. P., Read, S., Cooper, G. (1987) Identification of a receptor protein in cotton fibers for the herbicide 2,6-dichlorobenzonitrile. *Plant Physiol.* 84, 415–420.

Heim, D. R., Bjelk, L. A., James, J., Schneegurt, M. A., Larrinua, I. M. (1993) Mechanism of isoxaben tolerance in *Agrostis palustris* var. *Penncross*. *J. Exp. Bot.* 44, 1185–1189.

Heim, D. R., Roberts, J. L., Pike, P. D., Larrinua, I. M. (1989) Mutation of a locus of *Arabidopsis thaliana* confers resistance to the herbicide isoxaben. *Plant Physiol.* 90, 146–150.

Heim, D. R., Roberts, J. L., Pike, P. D., Larrinua, I. M. (1990a) A second locus, ixrB1 in *Arabidopsis thaliana*, that confers resistance to the herbicide isoxaben. *Plant Physiol.* 92, 858–861.

Heim, D. R., Skomp, F. R., Tschabold, E. D., Larrinua, I. M. (1990b) Isoxaben inhibits the synthesis of acid insoluble cell wall materials in *Arabidopsis thaliana*. *Plant Physiol.* 93, 695–700.

Heim, D. R., Skomp, J. R., Waldron, C., Larrinua, I. M. (1991) Differential response to isoxaben of cellulose biosynthesis by wild-type and resistant strains of *Arabidopsis thaliana*. *Pestic. Biochem. Physiol.* 39, 93–99.

Klimyuk, V. I., Carroll, B. J., Thomas, C. M., Jones, J. D. G. (1993) Alkali treatment for rapid preparation of plant material for reliable PCR analysis. Technical Advance. *Plant Journal* 3, 493–494.

Lefebvre, A., Maizonnier, D., Gaudry, J. C., Clair, D., Scalla, R. (1987) Some effects of the herbicide EL-107 on cellular growth and metabolism. *Weed Res.* 27, 125–134.

Schneegurt, M. A., Heim, D. R., Larrinua, I. M. (1994) Investigation into the mechanism of isoxaben tolerance in dicot weeds. *Weed Sci.* 42, 163–167.

Sharples, K. R., Hawkes, T. R., Mitchell, G., Edwards, L. S., Langford, M. P., Langton, D. W., Rogers, K. M., Townson, J. K., Wang, Y. (1998) A novel thiazolidinone herbicide is a potent inhibitor of glucose incorporation into cell wall material. *Pest. Sci.* 54, 368–376.

What is claimed is:

1. An isolated and purified mutant gene encoding a isoxaben resistant cellulose synthase comprising a cellulose synthase gene with a specified nucleic acid sequence, wherein the nucleic acid sequence comprises the nucleotide sequence of SEQ ID NO: 1.

2. An isolated and purified mutant gene encoding a isoxaben resistant cellulose synthase comprising a cellulose synthase gene with a specified nucleic acid sequence, wherein the nucleic acid sequence comprises the nucleotide sequence of SEQ ID NO: 4.

* * * * *